(12) United States Patent
Shepard

(10) Patent No.: US 6,751,342 B2
(45) Date of Patent: *Jun. 15, 2004

(54) SYSTEM FOR GENERATING THERMOGRAPHIC IMAGES USING THERMOGRAPHIC SIGNAL RECONSTRUCTION

(75) Inventor: Steven M. Shepard, Southfield, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 148 days.

This patent is subject to a terminal disclaimer.

(21) Appl. No.: 10/123,726

(22) Filed: Apr. 15, 2002

(65) Prior Publication Data

US 2002/0172410 A1 Nov. 21, 2002

Related U.S. Application Data

(63) Continuation-in-part of application No. 09/729,617, filed on Dec. 4, 2000, now Pat. No. 6,516,084.
(60) Provisional application No. 60/283,566, filed on Apr. 13, 2001, provisional application No. 60/284,649, filed on Apr. 18, 2001, provisional application No. 60/175,792, filed on Jan. 12, 2000, and provisional application No. 60/168,556, filed on Dec. 2, 1999.

(51) Int. Cl.[7] ................................................. G06K 9/00
(52) U.S. Cl. ........................... 382/141; 250/332; 374/10
(58) Field of Search ............................... 382/141, 143, 382/149, 152; 348/86, 125; 700/95, 212; 250/330, 332, 358.1, 341.6, 339.02, 339.14, 341.1; 356/51; 374/5, 10, 120, 121, 124; 209/577

(56) References Cited

U.S. PATENT DOCUMENTS

| 4,719,350 A | 1/1988 | Alm ........................... 250/330 |
| 5,032,727 A | 7/1991 | Cox, Jr. et al. ............. 250/330 |
| 5,631,465 A | 5/1997 | Shepard ...................... 250/330 |
| 5,711,603 A | 1/1998 | Ringermacher et al. ....... 374/5 |
| 5,963,662 A | 10/1999 | Vachtsevanos et al. ..... 382/150 |
| 6,033,107 A | 3/2000 | Farina et al. .................. 374/5 |
| 6,346,704 B2 * | 2/2002 | Kenway .................. 250/341.6 |

* cited by examiner

Primary Examiner—Samir Ahmed
(74) Attorney, Agent, or Firm—Rader, Fishman & Grauer PLLC

(57) ABSTRACT

A method and system for non-destructive, reference-free thermographic detection of sub-surface defects uses an infrared camera to capture multiple, spatially different images of a sample that has been heated and allow to cool to equilibrium temperature. The temperature-time data obtained for each pixel in each image is converted into the logarithmic domain and a least squares fit is conducted on the data to generate a polynomial expression corresponding to the temperature-time data for a given pixel. This polynomial expression can be transformed into the original time domain to obtain temperature-time data with improved signal-to-noise characteristics.

33 Claims, 14 Drawing Sheets

(Reconstructed)

(RAW)

(Reconstructed 1st Derivative)

(Reconstructed 2nd Derivative)

SYSTEM FOR GENERATING THERMOGRAPHIC IMAGES USING THERMOGRAPHIC SIGNAL RECONSTRUCTION

REFERENCE TO RELATED APPLICATIONS

This application is a continuation-in-part of U.S. application Ser. No. 09/729,617, filed Dec. 4, 2000, which claims the benefit of U.S. Provisional Application No. 60/168,556, filed Dec. 2, 1999 and Provisional Application No. 60/175,792 filed Jan. 12, 2000. This application also claims the benefit of U.S. Provisional Application No. 60/284,649 filed Apr. 18, 2001 and U.S. Provisional Application No. 60/283,566 filed Apr. 13, 2001.

TECHNICAL FIELD

The present invention generally relates to thermal imaging and more particularly relates to non-destructive detection of defects in a sample using thermographic image data.

BACKGROUND OF THE INVENTION

Active thermography is used to nondestructively evaluate samples for sub-surface defects. It is effective for uncovering internal bond discontinuities, delaminations, voids, inclusions, and other structural defects that are not detectable by visual inspection of the sample. Generally, active thermography involves heating or cooling the sample to create a difference between the sample temperature and the ambient temperature and then observing the infrared thermal signature that emanates from the sample as its temperature returns to ambient temperature. An infrared camera is used because it is capable of detecting any anomalies in the cooling behavior, which would be caused by sub-surface defects blocking the diffusion of heat from the sample surface to the sample's interior. More particularly, these defects cause the surface immediately above the defect to cool at a different rate that the surrounding defect-free areas.

As the sample cools, the infrared camera monitors and records an image time sequence indicating the surface temperature, thereby creating a record of the changes in the surface temperature over time. It is the current practice to use a human operator to view the record of these changes and to look for "hot spots" in the image record. In many instances, this analysis is purely visual (i.e. the human inspector views a display of the image output on a monitor and identifies regions that appear "hot" compared to surrounding areas. More sophisticated methods attempt to use numerical processing of the data by generating contrast curves relative to a reference specimen of known quality and composition (a so-called "gold standard"). This reference specimen, which is known to be defect free, is typically placed in the field of view of the imaging camera. In other instances, the "gold standard" is not a reference specimen at all, but rather it is an image that has been derived from a physical model. However, in general, the time history of the cooling of the sample is not viewed as a whole (i.e. a contiguous sequence), but rather as a collection of individual frames acquired from the infrared camera. These methods work adequately for large, or near surface, defects. However, as manufacturing processes and safety standards requirements place higher demands regarding smaller/more subtle defect detection, these traditional methods become less effective because the small signal levels associated with subtle defects are lost in the noise, drift, and instability that is inherent to infrared cameras. Also, visual defect identification methods tend to be subjective, and they do not readily and easily lend themselves to the automatic defect detection process. Further, it is not possible to measure the depth of the defects simply by viewing the infrared images.

There have been attempts to determine the depth of a defect via processing and analysis of the data from the infrared camera and also to automate the defect detection process. In some cases, the data from the infrared camera is transferred to a computer for processing and analysis to detect variations in the cooling behavior or to perform mathematical operations on the data to determine the depth of the sub-surface defect or other defect properties. These types of calculations, however, often require expensive low noise, high-speed digital infrared cameras. Further, the cumbersome nature of having a computer attached to the camera for conducting calculations makes the combination impractical for applications outside of a laboratory, such as field inspections.

Also, infrared data sequences of thermal decay typically used in non-destructive testing tend to be difficult to manipulate mathematically due to their low signal-to-noise ratios and large dynamic range and also require a great deal of computer processing power, memory and storage space.

One attempt at automating the defect detection process involves analyzing the contrast between each pixel in the image and a reference to generate a curve representing the amount of contrast between each pixel and the reference. The reference can be established any number of ways including using a reference pixel (from the sample image), a pixel group (from the sample image). If a pixel, or a pixel group is used, a reference point or reference area of the sample must be defined. The reference can be a defect-free area of the sample, or the mean of the entire field of view of the camera (when viewing the sample). The temperature-time history of this reference pixel or pixel group is subtracted from the time history of each pixel in the image to generate a contrast vs. time plot. Any significant temperature difference between any given pixel and the reference indicates the presence of a defect which will exhibit itself as a peak in the contrast vs. time plot. The contrast vs. time plot can be measured with respect to the time at which the peak occurs, the time at which a maximum ascending slope occurs, and/or a moment of the curve for each pixel. Other options, such as generating and displaying the contrast vs. time plot with a reference plot and checking the point at which the two plots separate, have also been applied.

Such contrast-based methods tend to have significant shortcomings, however. In addition to the data storage, memory and processing problems noted above due to the large size of the infrared image data files, contrast-based methods require the identification of a defect-free region on the sample as a reference point. This requirement is often not realistic for some samples if, for example, the size of the defect is larger than the infrared camera's field of view. In such a case, there is no defect-free area available that can act as a reference for a given region. Further, if the entire sample exhibits a defect (e.g., a large delamination running underneath the entire surface of the sample), there is no contrast between any region of the sample because the whole sample is equally or nearly equally defective.

Contrast-based methods that rely on the mean of the entire field of view as a reference have also been used, but this method assumes that the defect area in the field is small enough so that it will not appreciably influence the mean. If a defect (or group of defects) occupies a large portion of the field of view, the contrast method is ineffective because a significant portion of the mean value result is composed of data derived from defective sample points which acts to reduce any appreciable difference between the defect area and the mean when the contrast value is calculated.

Regardless of the specific reference value used in detecting defects, the results obtained using contrast-based methods depend strongly on the choice of reference region on the sample. More particularly, the results obtained in contrast-based methods can be altered by simply changing the location of the reference region.

Further, in evaluating the results from both the contrast-based methods and the data obtained directly from the infrared camera, identifying the time at which a maximum peak slope occurs (indicating the presence of a defect) is often difficult because the signals are often inherently noisy, thus the contrast based method must be capable of discriminating between pixels associated with defects and pixels associated with noise. Although the peak slope (of the temperature vs. time relationship) is a useful indicator of defect depth, the peak slope inherently must occur earlier than the peak contrast and may be obscured by the heating event, or by lingering heat from the equipment after flash heating the sample. The peak slope may also be obscured if the instantaneous temperature of the sample exceeds the camera's peak temperature detection capabilities, causing an initial, highly nonlinear response from the camera due to camera saturation.

A common approach to improving the signal-to-noise content of thermographic data is to replace the amplitude of each pixel with the mean or median value of that pixel and its surrounding nearest neighboring pixels as defined by an N×N matrix, where N is a selected integer. This approach, however, sacrifices spatial resolution to lessen temporal noise. Another approach for reducing temporal noise is to average data over a selected number of consecutive frames, but this approach sacrifices temporal precision. As a result, known techniques for reducing temporal and spatial noise necessarily degrade temporal and/or spatial resolution and precision.

Another technique which may be used in attempt to filter noise from thermographic data is to simply fit the raw temperature-time history of each data point of the sample, with a polynomial or a set of orthogonal functions. However, when one understands the underlying physical process of thermal imaging as well as the nuances of using all but the most expensive thermal imaging cameras, these approaches prove unsuccessful for several reasons:

A. Thermographic data (when generated using a pulse of energy to heat the sample), presents an extremely large dynamic range thereby making it extremely difficult to accurately fit both the data occurring early in the sampling process (large amplitude) and later in the sampling process (small amplitude). Specifically, the very steep, early post-excitation behavior of the temperature-time history of a point requires a high order polynomial or other similar expansion to accurately model the data. However, such high order terms introduce undesirable errors (such as oscillations) in the polynomial fit later in the time-temperature sequence when in fact the data is not oscillatory but rather stable.

B. The early, high amplitude response of the sample's thermal signature, is often outside, or near the calibration limit of the infrared camera. As a result, the signal generated during this portion of the imaging exercise is often highly non-linear.

C. The early, high amplitude, data points dominate the fit and worsen the fit for later occurring data points.

The difference between the thermal response of an intact point (i.e. a defect free portion of a sample) and the thermal response of a sub-surface defects is often very small (e.g. on the order of the temperal noise) and accordingly very difficult to identify.

OBJECTS OF THE INVENTION

Accordingly, it is an object of the invention to provide for a non-visual interpretation of thermographic data and to permits the objective, non-destructive evaluation of samples.

Accordingly, it is a further object of the invention to provide a non-destructive system for detecting sub-surface defects in a sample wherein an extremely high quality representation of heat flow within a sample is generated and artifacts of that signal due to electronic noise, mechanical instability of the imaging apparatus, or random thermal signals, are rejected.

Another object of the invention is to provide a non-destructive defect detection system and method that reduces the size and complexity of the temperature-time history of image data without compromising the usefulness of the data in detecting the location and physical characteristics of sub-surface defects of a sample.

Still another object of the invention is to provide a non-destructive defect detection system that does not require obtaining a reference value to detect defects by locating areas in which there is a contrast between the reference and the sample being evaluated.

Yet another object of the invention is to provide to improve both the temporal and spatial signal-to-noise ratio of an infrared camera output without sacrificing temporal or spatial resolution of the data generated therefrom.

An additional object of the invention is to image multiple segments of a sample and then to assemble the multiple segments to form an integrated, mosaic image.

SUMMARY OF THE INVENTION

Accordingly, the present invention is directed to a system for determining a time response of a monotonically changing characteristic of a sample, including a camera that obtains at series of sample images over time, wherein each image includes a plurality of pixels, and each pixel includes an amplitude corresponding to the monotonically changing characteristic of a portion of the imaged sample, and a processor that receives the series of sample images and generates therefrom a data array for each portion of the imaged sample, wherein the data array is a reconstructed version (model) of the pixel amplitude image data, as a function of time, and wherein the processor generates the reconstructed version of the raw image data by fitting a polynomial (or similar mathematical expansions or decompositions—such as those used with orthogonal functions) to at least some of the pixel amplitude image data, the polynomial having at least one polynomial coefficient such that each portion of the imaged sample is represented by a coefficient array containing said at least one polynomial coefficient, and wherein the processor generates from the coefficient array, a reconstructed thermal image of at least part of said sample.

The invention is also directed to a method for determining a time response to a monotonic change in a thermal characteristic of a sample, comprising the steps of obtaining a plurality of spatially distinct images (images taken over different regions of the sample) of the sample over time, each spatially distinct image having a plurality of pixels each pixel having an amplitude corresponding to the monotonically changing characteristic of a portion of the imaged sample, the sample, generating a data array for each pixel amplitude respectively corresponding to a portion of each spatially distinct image of the sample, the data array corresponding to a scaled version of the pixel amplitude at a given time or to a scaled version of the given time, fitting a polynomial to the data array associated with at least a portion of the plurality of pixels, the polynomial having at least two polynomial coefficients, such that each pixel amplitude respectively corresponding to a portion of each spatially distinct image of the sample is represented by a coefficient array containing said at least two polynomial coefficients, generating a plurality of reconstructed images corresponding to the plurality of spatially different images, and forming an image mosaic from the reconstructed images.

BRIEF DESCRIPTION OF THE DRAWINGS

FIG. 8B is a temperature-time graph of raw data generated by regions A, B, and C of the control sample 104' of FIG. 8A as it cools, wherein the data is displayed in the linear domain.

DETAILED DESCRIPTION OF THE PREFERRED EMBODIMENTS

General

Figure 1:
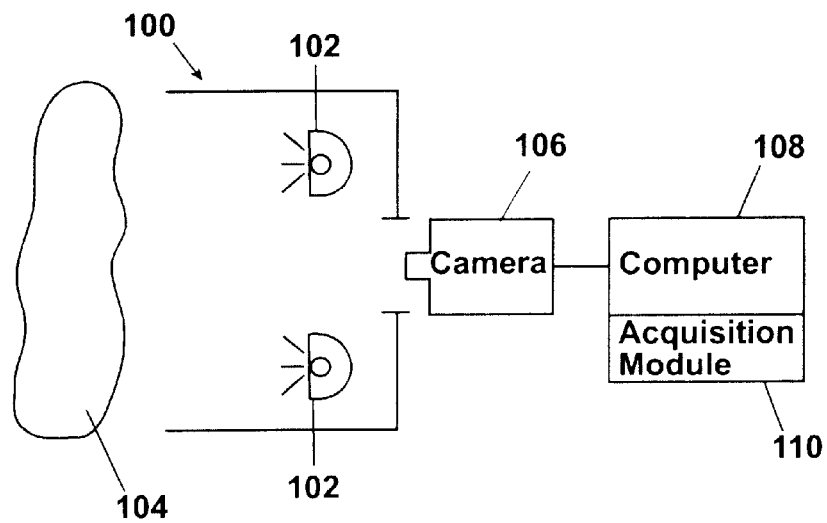
FIG. 1 is a block diagram of one embodiment of the present invention wherein the thermal excitation source is a light source and the sample 104 is a generic sample.

The system of the present invention operates on a reconstructed representation of the entire temperature-time history of acquired thermographic data rather than the raw thermographic data. This approach is beneficial because:

A. The reconstructed representation of the temperature-time history of the thermographic data is typically an order of magnitude smaller than the raw thermographic data in terms of the amount of computer memory it requires for storage.

B. The reconstructed representation of the thermographic data is almost entirely free of temperal noise (typically introduced from the infrared camera) and mechanical instability. There are several possible sources of mechanical instability associated with using infrared cameras. Infrared cameras require cooling to very low temperatures (typically infrared cameras are cooled with liquid nitrogen using a Stirling engine). A Stirling engine employs, amongst other components, a small oscillating piston. Because the piston oscillates, it gives rise to camera vibrations. It is difficult to completely eliminate these vibrations even with the most steadfast of mounting apparatus (which is impractical to use in some applications). Moreover, the vibrations can become amplified if the camera is mounted to a tripod or lever arm. In practice, some applications can not be carried out unless the inspection device (infrared camera), is held in place by the operator while data is acquired. Any shaking or movement by the operator will be reflected in "mechanical instability" of the data.

C. The reconstructed representation of the thermographic data is, in a preferred embodiment, based on an analysis of derivatives (rather than contrast relative to nearby points) of the time evolution of each point in the image. Analyzing derivatives lends itself to directly automating the image inspection task because they can be objectively analyzed for characteristic features (zero crossings, extrema, etc.) without visual confirmation by an operator.

D. The disclosed system requires no a priori knowledge of the physical characteristics of the sample. A priori knowledge is not necessary because the nature of the reconstructed representation of the thermographic image (taken from defect free samples) differs only in scale from sample to sample (there is no deviation in shape from sample to sample).

E. The present system is based on a well-known physical model that allows analysis of a sample response to excitation as a deterministic phenomenon and not a phenomenon which is linked to thermographic data collected from neighboring points.

The present invention detects subsurface defects of a sample using an infrared camera by observing and analyzing selected characteristics of a thermal decay process of the sample. The basic foundation in which the inventive system operates assumes that the field of view is limited to the portion of interest on the sample and that inspection of the total sample surface may require interrogation of multiple regions (also called image segments herein). Further, the inventive system and method recognizes that a thermally excited (heated) region of the sample cools monotonically after the excitation source removed until the sample reaches thermal equilibrium with its surroundings, and that the thermal response of any point on the sample surface during the time interval immediately after heating, decays in such a manner that the natural logarithm of the temperature-time response of a defect-free sample, as it cools, is a function that can be approximated by a straight line.

First Discussed Hardware Embodiment

Figure 2:
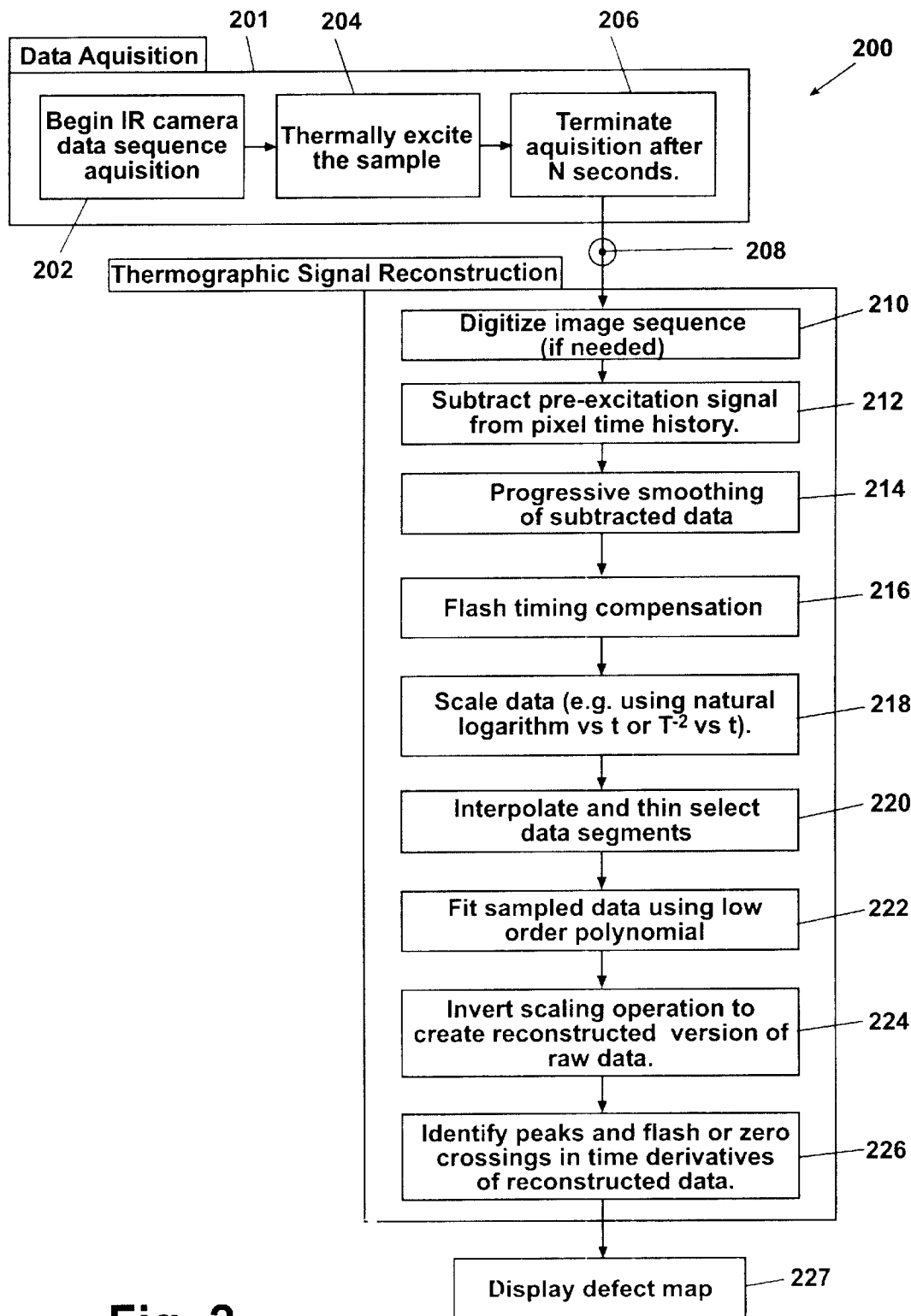
FIG. 2 is a flowchart illustrating an embodiment of the data reconstruction method of the present invention.

FIG. 1 illustrates one possible embodiment of the apparatus used to carry out the invention, while FIG. 2 is a flowchart illustrating one embodiment of the inventive method. Referring to FIG. 1, a system 100 for obtaining the data to be analyzed in the inventive method includes at least one heat source 102, and preferably a pulsed heat source, that heats a sample 104 to be evaluated with a pulse. The heat source itself can be any source, such as flashlamps, heat lamps, electric current, heated air, electromagnetic induction, ultrasonic energy, etc., but the specific choice of heat source does not matter for purposes of the invention as long as there is a heating of the sample and then a monotonic, deterministic decrease in the sample's temperature. An infrared camera 106 captures a series of images of the sample, and is coupled to a computer 108 having digital image acquisition or analog frame-grabbing capabilities to convert the data from the infrared camera 106 to a format that can be analyzed and mathematically manipulated by the computer 108. Note that the computer 108 does not necessarily need to be separate from the camera 106 and that the functions in the computer 108 can be incorporated into the camera itself as, for example, an on-board integrated circuit. In fact, because the methods set forth herein greatly reduce the data volume and manipulation normally associated with image thermography, the methods set forth in this present invention make it particularly well suited to employ the image processing techniques of the present invention directly within a dedicated processor located within camera 106. The computer 108 may also have an optional acquisition module 110 that is used if the camera 106 obtains multiple spatially different images to generate a complete mosaic image of the sample, particularly when the sample is too large to fit in a single image frame.

Data Reconstruction Methodology

Referring now to the flowchart in FIG. 2, the inventive method 200 first involves starting acquisition of a sequence of infrared images from the sample at step 202 and then thermally exciting the sample 204. The image sequence can be stored in computer memory, videotape, or any other electronic storage means. The acquisition process is terminated after a predetermined time 206 and digital data corresponding to the image sequence is transferred 208 to a computer or dedicated hardware for mathematical analysis.

If the data is in analog format, it is first digitized at step 210. The length of the image sequence will depend on the type of material being inspected and the depth at which suspected defects are located. If the material has low thermal conductivity and/or if the suspected defects are relatively deep inside the sample, the image sequence may be lengthened. A typical image sequence from an infrared camera operating at 60 frames per second will contain several hundred frames. In extreme cases, the image sequence may contain as many as several thousands of frames. The time over which the data acquisition step 201 takes place can range over several seconds as the sample temperature returns to equilibrium, but the specific length of time will vary depending on the thermal properties of the sample. Further, the output image sequence (or defect map sequence) can be generated over any time duration bounded between the heating flash event and the last image sequence acquisition event, independent of the sampling rate of the infrared camera 106.

In step 212 the pre-excitation temperature amplitude of each pixel is subtracted from the post-excitation history temperature for that pixel. The process is applied to every pixel in the field of view of every image in the image sequence. The result of subtracting the pre-excitation temperature is that the resulting signal indicates the sample's response to the thermal excitation event and negates any influence that the sample's ambient temperature prior to excitation might otherwise have on the data.

Next, in step 214, the subtracted data is smoothed using any number of smoothing techniques. Smoothing is necessary because although the overall trend of the surface temperature of the sample is monotonically decreasing, consecutive data points in the post-excitation time history may not behave as expected due to undesirable noise artifacts. These undesirable noise artifacts typically are composed of high frequency components and are easily removed by fitting a straight line segment (or second order polynomial) to groups of adjacent points and replacing a particular point with the value on the straight line. This process is preferably repeated for every point in the time history; however, the number of points chosen in each grouping should increase as the latter occurring data is smoothed. This allows each line segment to become longer as later points occurring later in the time history are smoothed. This approach accurately models the later occurring data primarily because as time extends further away from the onset of the thermal pulse, the image data tends to change less than it did earlier in time and accordingly behaves more linear.

In step 216, flash timing compensation is carried out. This is primarily necessary because the one-dimensional heat flow model used as a theoretical basis in this application, assumes that the sample is heated instantaneously by a heat pulse which is infinitesimal, and that this heat pulse occurs at time=$t_o$. In practice, the duration of the heat pulse is finite, and may occur between video frames. The result is a deviation from linearity in the earliest data points in the post-flash time history. By subtracting a time increment from every pixel that is equivalent to the time delay difference between t=0 and the peak of the excitation signal, the early non-linearity is removed. This technique amounts to synchronizing the frame of the camera with the flash event of the heat pulse. If this non-linearity is not compensated for, it manifests itself in a "kink" in the graphical representation of the early segment of the data.

Figure 3A:
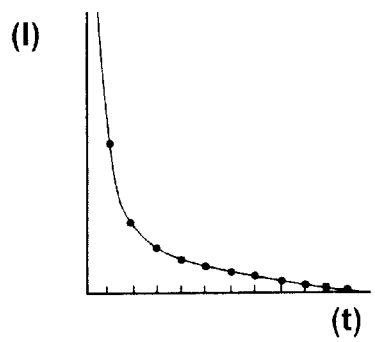
FIGS. 3A and 3B are thermal decay graphs illustrating a temperature-time decay characteristic of an imaged sample in a linear domain (FIG. 3A) and in a logarithmic domain (FIG. 3B)
Figure 3B:
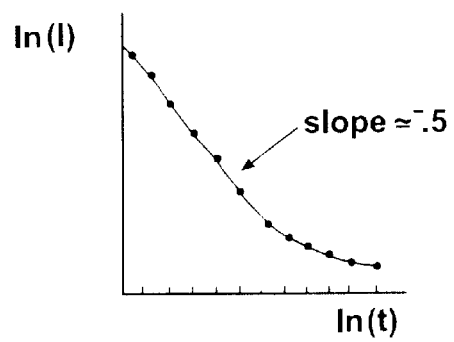

In step 218, the data is scaled. Preferably the data is scaled in a way which reduces the dynamic range of the post-flash time history and causes it to behave in a linear, or near linear, manner if no sub-surface defects are present. One such preferred scaling operation is using the natural logarithm of the temperature versus natural logarithm of time plot (see FIG. 3A of prescaled data and FIG. 3B of post scaled data). This approach is preferable because it results in a temperature versus time plot of a defect free sample to be a straight line with a slope of −0.5 (the slope is the same irrespective of the sample composition or hardware used in the imaging process). However, other scaling operations are possible. For example, scaling by using the inverse square of the temperature ($T^{-2}$) versus time results in an ascending straight-line result for a defect-free sample. In either case, the behavior follows the predictions of a one-dimensional solution of the heat diffusion equation.

Next, in step 220, the post-excitation response of the sample is governed by diffusion of heat into the sample and this diffusion of heat is described by the well-known diffusion equation. As a result, the surface temperature changes rapidly immediately after excitation, but the rate of change decreases as time progresses (see FIG. 3A). If data is acquired at a constant (frame) rate, the abrupt decay occurring in the early stages of the sample cool down causes there to be too few early time data points and an excessive number of later data points (this is clearly seen in the plot of temperature decay versus time of FIG. 3A). A more accurate way to model the true thermal behavior of the sample is to add reconstructed points by interpolation between early raw data points in order to increase the influences of early behavior in the fit. Also, improved fidelity to the underlying data is achieved if latter data points are sampled in a way which reduces the influence of the latter occurring data points (typically this is accomplished by thinning later occurring data points).

Step 222 involves fitting the data generated in step 220 using a low order polynomial (preferably sixth order or less) using a leased squares fit technique. Note that the disclosed method fits a polynomial to the natural logarithm of the temperature-time data and not to the actual (raw) temperature-time data in the linear domain. The low order polynomial serves as a low pass filter to ensure that only the information content of the data representing the thermal response of the sample is preserved and that the noise content of the data is rejected. The use of as low order polynomial as possible is counter intuitive but nonetheless it is the preferred method. Generally speaking, a higher order polynomial will allow you to fit the data with less error. However, because the source of the data is a thermal event (which are low frequency events), any high frequency information contained in the data can be confidently dismissed as noise and such high frequency noise can be easily filtered out using the lowest order polynomial which still permits reasonable fidelity to the underlying thermal information contained in the data. The resulting function for the amplitude for a given pixel at location i, j (i=row, j=column) is defined as:

$$\ln[I_{ij}(t)] = a_0 + a_1\ln(t) + a_2[\ln(t)]^2 + \ldots + a_n[\ln(t)]^n \quad (1)$$

In step 224, the scaling is inverted to create a reconstructed version of the new data. Specifically, the inverse of the operation used in step 218 to scale the data is, performed on the polynomial representation of the time history that is created in step 222. Accordingly, if we scaled the data using natural log scaling, we would invert the process by operating on the data using the following formula:

$$I_{ij}(t) = \exp\{\ln([I_{ij}(t)])\} \quad (2)$$
$$= \exp\{[a_0 + a_1\ln(t) + a_2[\ln(t)]^2 + \ldots + a_n[\ln(t)]^n\}$$

Likewise if we scaled the data using the $T^{-2}$ operation, we conduct an inverse operation to invert the $T^{-2}$ operation.

As can be seen from equation 1, the polynomial resulting from step 222 is a continuous function obtained from the discrete data, and thereby allows the method of the present invention to generate pixel amplitude values for all time values (even for time values that fall between frame acquisitions). Once the polynomial has been generated in step 222 for each pixel, each pixel is represented by an array of n polynomial coefficients, which will typically be six coefficients or less making it unnecessary to thereafter store the actual data sequence which can be several hundreds or even several thousands of frames generated by the infrared camera. Because of the polynomial representation includes only an array of coefficients, and because the polynomial representation of the pixel temperature-time characteristic is independent of the length of the data sequence, the amount of data that must be stored for any given pixel is tremendously reduced by the polynomial representation and accordingly, much simpler to manipulate mathematically than raw camera data. The resulting file size for storing the pixel data is independent of the number of images taken by the camera, further reducing the memory needed to store or manipulate the image data. For example, in one embodiment, the file size is equal to the number of pixels being imaged multiplied by the number of coefficients in the polynomial multiplied by the number of bytes per coefficient, regardless of the number of images. The result of transforming the polynomial function from the logarithmic domain back to the linear domain, is a reconstructed temperature-time curve that has a significantly higher signal-to-noise ratio than the original raw signal, making it more suitable for signal analysis.

Figure 4:
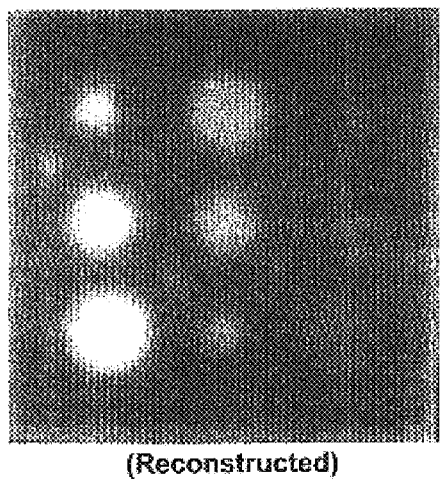
FIG. 4 is an image (formed from reconstructed data) of a front view of a control sample, wherein the control sample contains a plurality of flat bottom holes drilled from the back of the sample at various depths.

In step 226, the reconstructed data is analyzed to determine if any sub-surface defects are present. This determination can be done in any number of ways. Firstly, the reconstructed data for each pixel can be assembled into an image which is displayed graphically to a user. Such an image is known as a defect map and an example is depicted in FIG. 4. FIG. 4 is a front view of a control sample which has a plurality of flat bottom holes drilled into the sample from the back side. The holes are drilled at various depths (none of which pass through the sample) and accordingly manifest themselves in a reconstructed image as circular elements of various light intensities. These bright spots are also called "hot spots".

Figure 5:
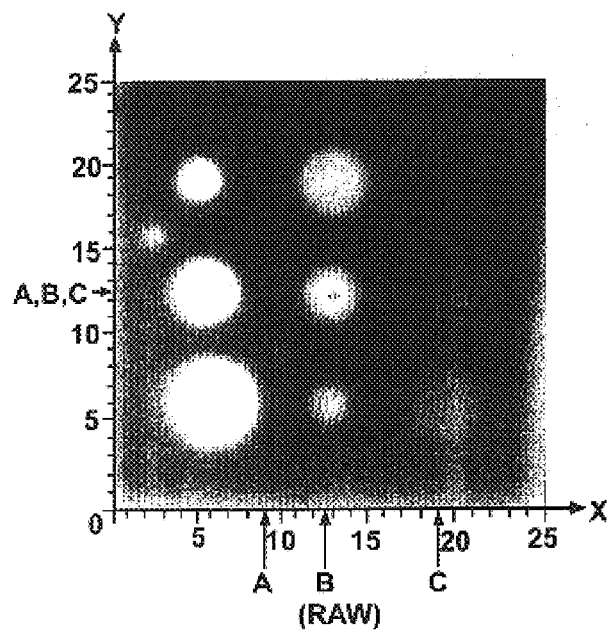
FIG. 5 is an image (formed from raw data, i.e. data that has not been conditioned using the reconstruction techniques of the present invention) of a front view of a control sample

FIG. 5 is a depiction of the same sample shown in FIG. 4; however, the depiction in FIG. 5 is constructed from raw thermographic image data wherein the image of FIG. 4 is assembled using reconstructed thermographic image data derived from the process described in FIG. 2. Rather than simply visually analyzing the reconstructed data, in some applications is far more convenient to examine the first, second, and even third time derivatives of the reconstructed data.

More particularly, if the reconstructed data is represented as:

$$f(t) = \exp\left[\sum a_1 \left[\ln(t)\right]_{i=0}^{N}\right] \quad (11)$$

the first derivative can be exp $$f'(t) = t^{-1}[\Sigma i a_i [\ln(t)]^{i-1}]f(t) \quad (4)$$

and the second derivative can be expressed as:

$$f''(t) = t^{-1}[\Sigma i a_1 [\ln(t)]^{i-1}]^2 f(t) + t^{-2}\{[\Sigma i(i-1)a_i[\ln(t)]^{i-2}] - [i a_i[\ln(t)]^{i-1}]\}f(t) \quad (5)$$

Images of the first and second derivatives (and other higher order derivatives) can be generated from Equations 4 and 5 through any means, if desired, by entering time information into the polynomial or its derivatives. Note that because the derivatives of the image data are calculated analytically rather than by fitting a straight line to the tangent of the noisy image data, the results obtained from the calculated derivatives yields more accurate results than attempts to compute the average over many noisy data points. Further, analytical calculation of the derivatives yields results that are true instantaneous derivatives rather than differentials over an interval spanning several image frames.

Also note that it is not necessary to convert the expressions back to their graphical format in order to glean useful information therefrom, it is sufficient to isolate and manipulate the arguments from expressions (3) and (4) to yield valuable information.

Because the invention focuses on differentiating and analyzing the polynomial function instead of the raw image data, obtaining information about the thermal characteristics of the sample is much simpler because differentiating the polynomial representation is less computationally complex than differentiating a noisy signal. More particularly, operating on the coefficients of the polynomial, and not on the original data, eliminates the need to manipulate hundreds or even thousands of separate images, greatly improving the speed in which the image data can be analyzed. Also, because the first and second derivatives are obtained by manipulating the polynomial expression rather than conducting linear regression or curve fitting, the derivatives do not themselves contribute any noise to the final result. Further, because the invention uses noise-reduced, analytically differentiated data obtained from scaled data, the noise reduction provided by the invention allows more accurate detection of deeper and weaker defects as well as large defects encompassing the entire field of view.

Figure 6:
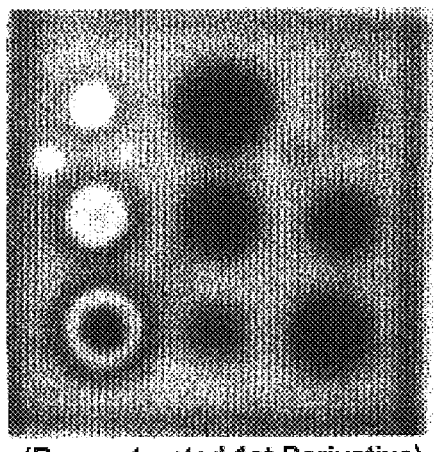
FIGS. 6 and 7 are images created by respectively taking the first and second derivative of the reconstructed data used to form the image of FIG. 4.
Figure 7:
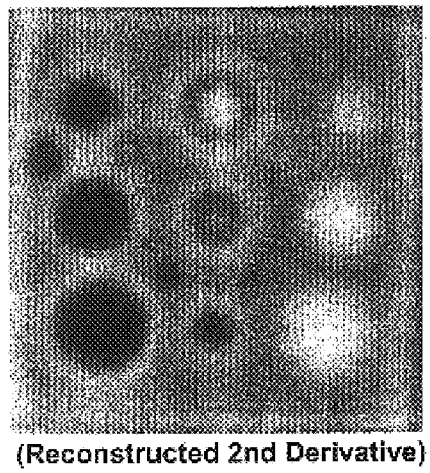

Because the reconstruction process of the present invention generates polynomials for each imaged portion of the sample, calculation of time derivatives of each polynomial is extremely straightforward. FIG. 6 is an image formed from the first derivative of the reconstructed data shown in FIG. 4. FIG. 7 is an image formed from the second derivative of the reconstructed data of FIG. 4. Third and higher order derivatives can be calculated and displayed using the identical techniques. One primary advantage for using derivatives of reconstructed data (as opposed to the reconstructed data itself), is that inflection points (or extrema) which occur as a result of the interaction of heat flow with sub-surface features are significantly enhanced in the derivatives despite the fact that they may be largely unnoticeable in the raw signal. This feature of the present invention is best explained in conjunction with FIGS. 5, and 8A–13.

Figure 8A:
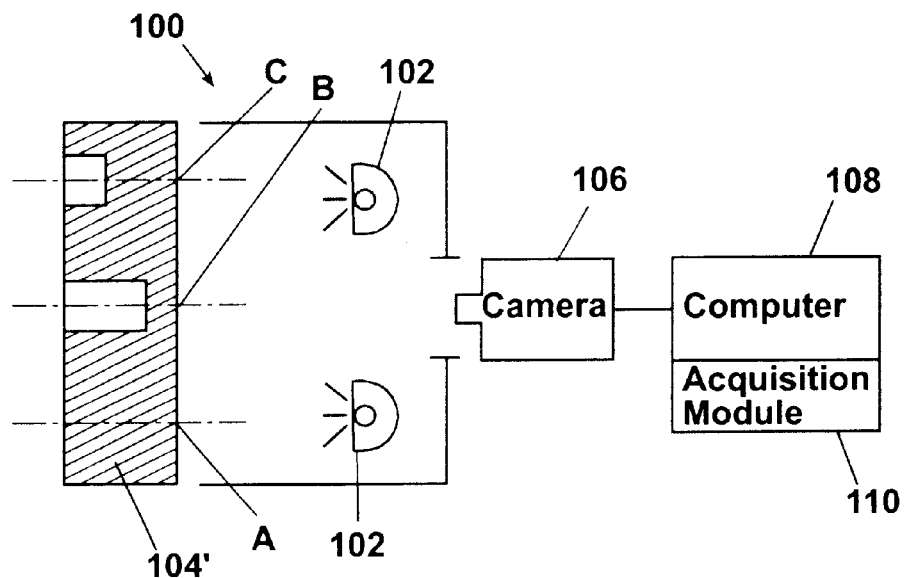
FIG. 8A is a block diagram of a test set up of the system of FIG. 1, wherein the sample 104' is a control sample.
Figure 8D:
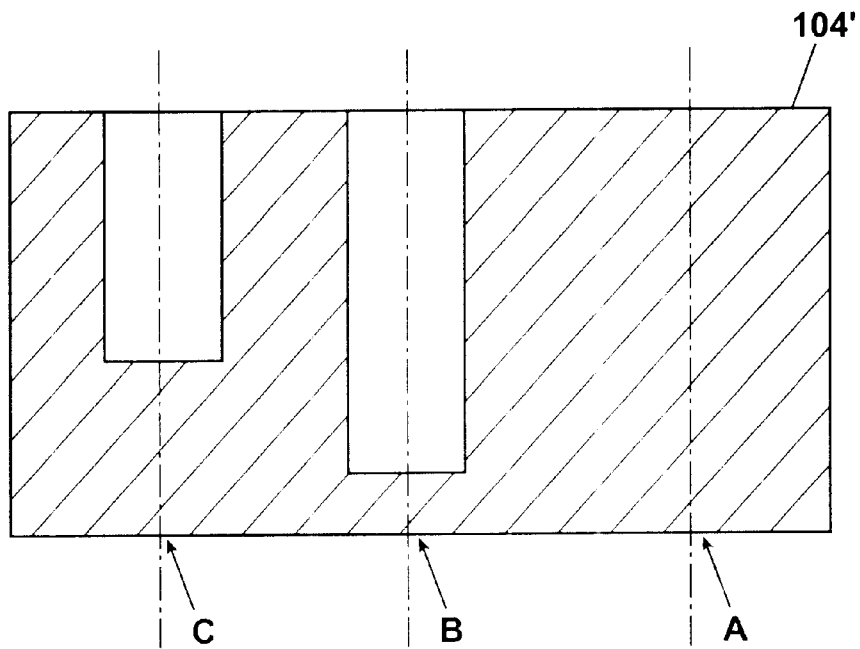
FIG. 8D is an enlarged view of the control sample 104' of FIG. 8A.
Figure 8C:
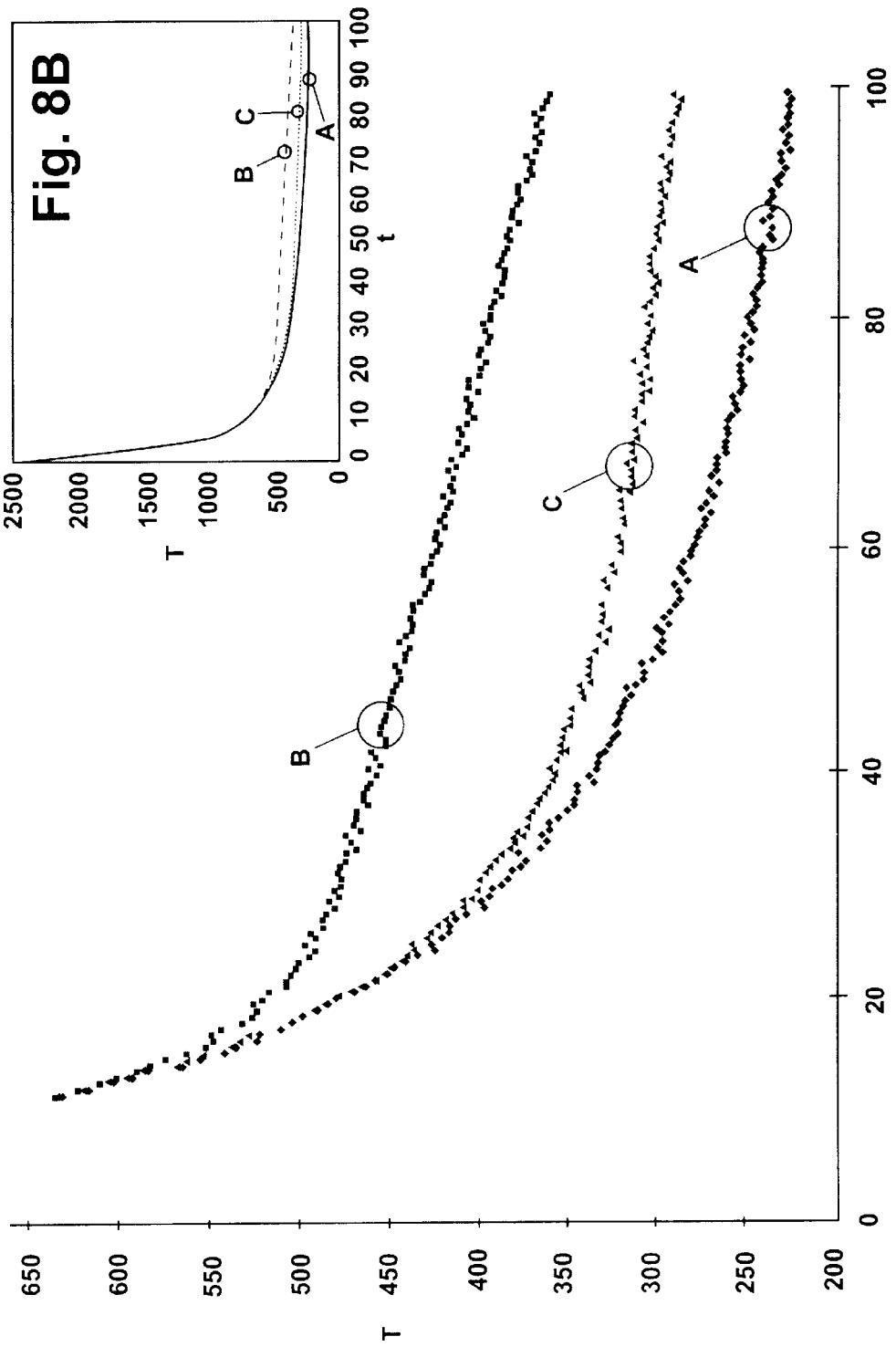
FIG. 8C is an enlargement of a portion of the graph of FIG. 8A.

FIG. 5 depicts (as seen on a graphical display device such as a cathode ray tube) a defect map constructed from raw data (data which has not been acted on by the method set forth in FIG. 2). The raw data of FIG. 5 has been collected from the control sample 104' as shown in FIG. 8D. The temperature—time history associated with three distinct points A, B, and C having Cartesian coordinates (9, 12.5); (12.5, 12.5); and (19, 12.5) respectively, is shown in FIG. 8B and a portion of FIG. 8B is enlarged in FIG. 8C. The numerous "wiggles" in the graph of FIG. 8C are examples of noise in the data and do not represent a thermal event in the control sample 104'. In the image of FIG. 5, the sample taken at region A contains no defect, the sample taken at B contains a relatively shallow defect and the sample taken at C contains a deeper defect. FIG. 8B is a temperature-time graph of the raw data generated by points A, B, and C as they cooled.

Figure 9A:
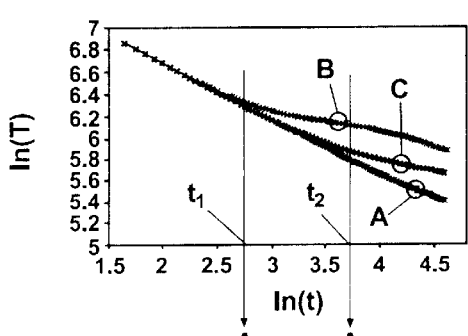
FIG. 9A is a temperature-time graph of raw data generated by regions A, B, and C of the control sample 104' of FIG. 8A wherein the raw data has been acted on by steps 202–220 of FIG. 2, but before it has been fit to a low order polynomial.

Now referring to FIGS. 9A–9E, the data sampled at points A, B, and C is acted on by steps 202 through 220 of the method set forth in FIG. 2 (and scaled using a ln/ln method), the graphical response for points A, B, and C is set forth in FIG. 9A. Next, the data is acted upon by step 222 and is graphically depicted in FIG. 9B in its reconstructed format. Note how noise free the data is in its reconstructed format. As can be easily seen in FIG. 9B, the thermal decay trace of points A, B, and C is almost identical until time $t_1$, is reached. At $t_1$, the thermal decay of point B does not continue to fall (cool) as quickly as the thermal decay of points A and C and accordingly point B breaks away from the general linear descent of points A and C and creates a "knee" in its descent pattern. Note that although this "knee" is made obvious by its breakaway from the graph of points A and C, it still would be noticeable by itself and accordingly the detection of the flaw associated with point B does not depend on plotting some other reference traces. Likewise the flaw associated with point C is also detectable without necessitating the presence of reference line A (although the presence of reference line A does make the "knee" at time=$t_2$ in graph C very obvious). Thus, it is clear to see that even subtle defects in a sample can be easily detected by looking for a break or "knee" in the data reconstructed according to the method of FIG. 2.

Figure 9B:
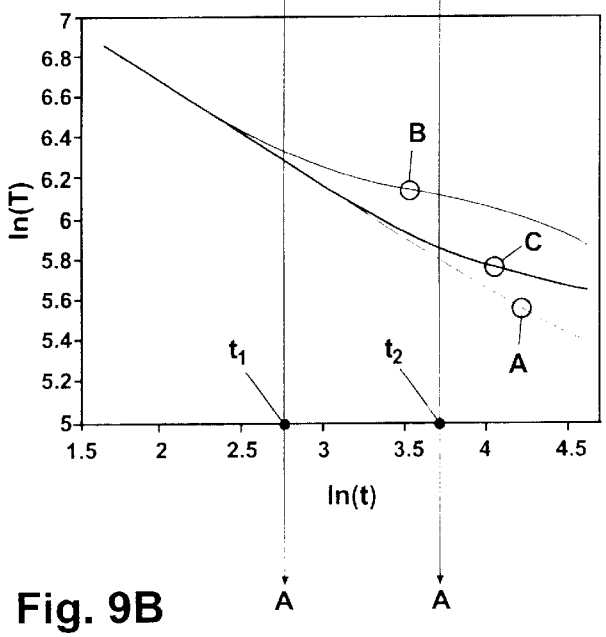
FIG. 9B is a graph of FIG. 9A after it has been acted upon by step 222.

Identifying defects is made even more easier than that discussed in conjunction with FIG. 9B when first, second, and third derivatives of the reconstructed data are used.

Figure 9C:
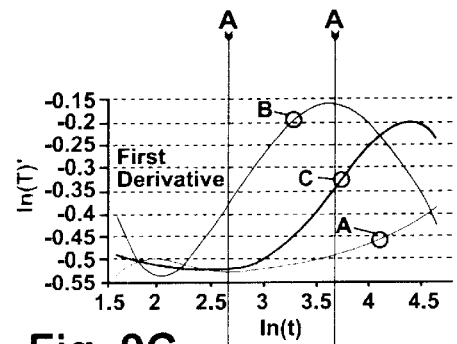
FIG. 9C–9E are graphical representations of the first, second, and third derivatives of the graph of FIG. 9B.
Figure 9D:
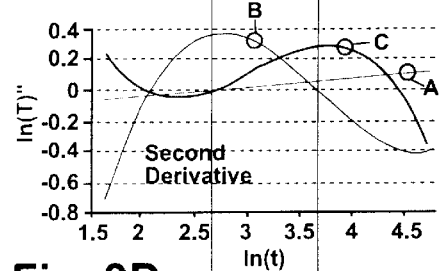
Figure 9E:
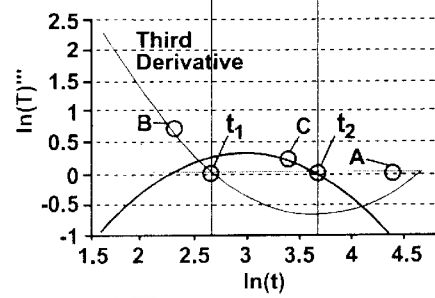

Specifically, FIGS. 9C–9E show the first derivative, second derivative, and third derivative respectively of the reconstructed data of FIGS. 9B. The third derivative of FIG. 9E makes it extremely easy to detect the occurrence of a flaw because such occurrences take place every time that a third derivative of points B and C makes a negative going zero crossing with the third derivative of point A.

Figure 10:
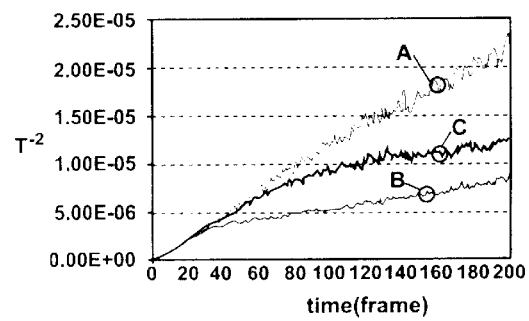
FIG. 10 is a graph of the same data used to generate FIGS. 8B and 8C except it is scaled using a $T^{-2}$ scaling scheme.

FIG. 10 contains the same data as that contained in FIG. 9A except the data in FIG. 10 is scaled according to the $T^{-2}$ scaling method discussed in conjunction with method step 218 of FIG. 2 whereas the scaling in FIG. 9A is constructed with respect to the ln/ln scaling step previously discussed in conjunction with step 218 of FIG. 2.

Although it has been illustrated in conjunction with FIGS. 9A–9E that the present invention is effective for finding defects in samples without the use of a control sample or some other reference, it is acknowledged that in some applications, it might be convenient for control samples or other references to be used. The method set out herein can be used in such applications; however, such an approach is wholly optional.

Specifically, the inventive system and method of generating polynomial equations from the image data may also be used to generate a contrast curve by identifying a defect-free reference region of the sample or using a separate reference sample and deriving the polynomial equation associated with the reference, if desired. A contrast curve can then be generated by subtracting the polynomial expression for the reference from the polynomial expression for each pixel; a large difference between the two would indicate the presence of a defect. If no reference is available, one can be created by extrapolating a straight line with a slope of –0.5 from the beginning of the reconstructed data curve.

Once steps 201 through 226 have been conducted for every pixel at a given time t, an image representation 227 of the behavior of the sample at that time can be scaled to match the dynamic range of the display device. This scaling operation can be conducting using any common statistical scaling algorithm.

The image 227 or images based on the polynomial and/or its derivatives can be displayed on an output device, such as on a computer display screen. The display screen can be one or more discrete points on the sample (FIG. 9B), a single reconstructed image at a selected time t (FIG. 4) or a sequence of reconstructed images displayed as a movie (not shown). The temporal resolution of the movie can be different than the actual data acquisition frame rate, if desired, to show the changes in the sample temperature more clearly; this can be conducted easily because the derived polynomial is a continuous function, as noted above.

The particular manner in which the sample is thermally excited and in which the data is obtained for polynomial fitting is not crucial to the invention and can be obtained in any number of ways well known to those skilled in the art. For example, the data can be obtained from temperature-time data in an image that is scanned (e.g., systems that acquire image data as the sample is moved relative to a heat source and an IR camera at a constant velocity, systems that move the camera and heat source relative to the sample, etc.).

Figure 11:
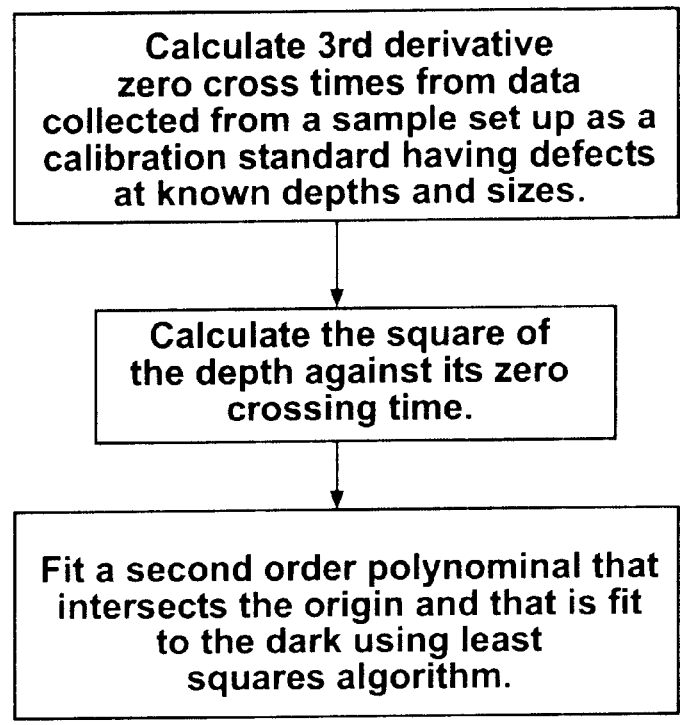
FIG. 11 is a flowchart illustrating one way in which the inventive system can be calibrated to detect and quantify the depth of a defect in a sample.

FIG. 11 is a flowchart illustrating how the generated polynomial is used in quantifying defect depth. Using a calibration standard (constructed from the same material as the sample of interest and possessing defects at known depth), the third derivative zero cross times are measured. For each known defect, the square of the depth is plotted against its zero crossing time and the second order polynomial that intersects the origin is fit to the data using a least squares algorithm. The net result is an expression for depth as a function of zero crossing time:

$$Depth = (a_0 + a_1 t + a_2 t^2)^{1/2} \quad (6)$$

Once this calibration has been performed, the coefficients $a_0$, $a_1$, and $a_2$ can be used for subsequent depth measurements on samples made from the same material as that of the calibration standard.

Other simpler calibration methods may be suitable in some applications (such as using a single known calibrated defect to do a one time calibration), however, such simple approaches only allow for a straight line fit. In order to achieve better accuracy and dynamic range (ability to detect both shallow and defects), using the calibration standard fashioned with defects at several depths and a second order polynomial fit (as described above) provides excellent results.

Figure 12:
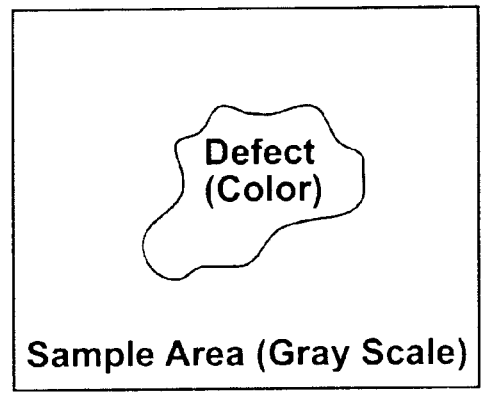
FIG. 12 is a graph illustrating an example of how the inventive system can be used to construct a color defect map.

The process set forth above in FIG. 11 is repeated for all the pixels and an image defect map is created therefrom. Pixels that do not have any negative going third-derivative zero crossings may be mapped to a selected color or displayed at a gray scale value that is proportional to the pixel amplitude at a particular time after flash heating. Preferably, the resultant defect map array will show the defects in colors that correspond to the depth of the defect and that are superimposed on a uniform selected color or gray scale image of the sample showing the normal sub-surface structure of the sample. A representative example of such a defect map is shown in FIG. 12.

If the system has been calibrated according to FIG. 11, the invention can then determine the defect depth. To determine the defect depth, the system uses $a_0$, $a_1$, and $a_2$ corresponding to the material composition of the sample. Constants, $a_1$, $a_2$, and $a_3$ are calculated from the temperature-time information of a defect having known dimensions (i.e., $a_0$, $a_1$, and $a_2$ can be readily calculated from Equation 6 if the second-derivative zero crossing time and the depth are known for a reference defect). To determine the defect area, the total number of pixels having third-derivative zero-crossing values are counted and multiplied by the single pixel area. The ability to accurately calculate defect area value can be of significant value because the criteria for rejecting a sample is often based on the defect area.

As can be seen above, no reference value is required to detect sub-surface defects (a reference is only required if quantitative measurements of thickness is required; however, defects can be detected from an image without using a reference). As a result, the invention can detect defects even in a sample that has a defect spanning the entire sample.

The above process can be used to pre-process any images from an infrared camera for further analysis, such as peak slope or peak contrast time measurements, breakpoint analysis, pulse phase lock-in, etc. The pre-processing steps described above generate an image signal with much of its temporal noise removed, yielding more accurate results in any additional processes.

Pulse Phase Reconstruction

Figure 13:
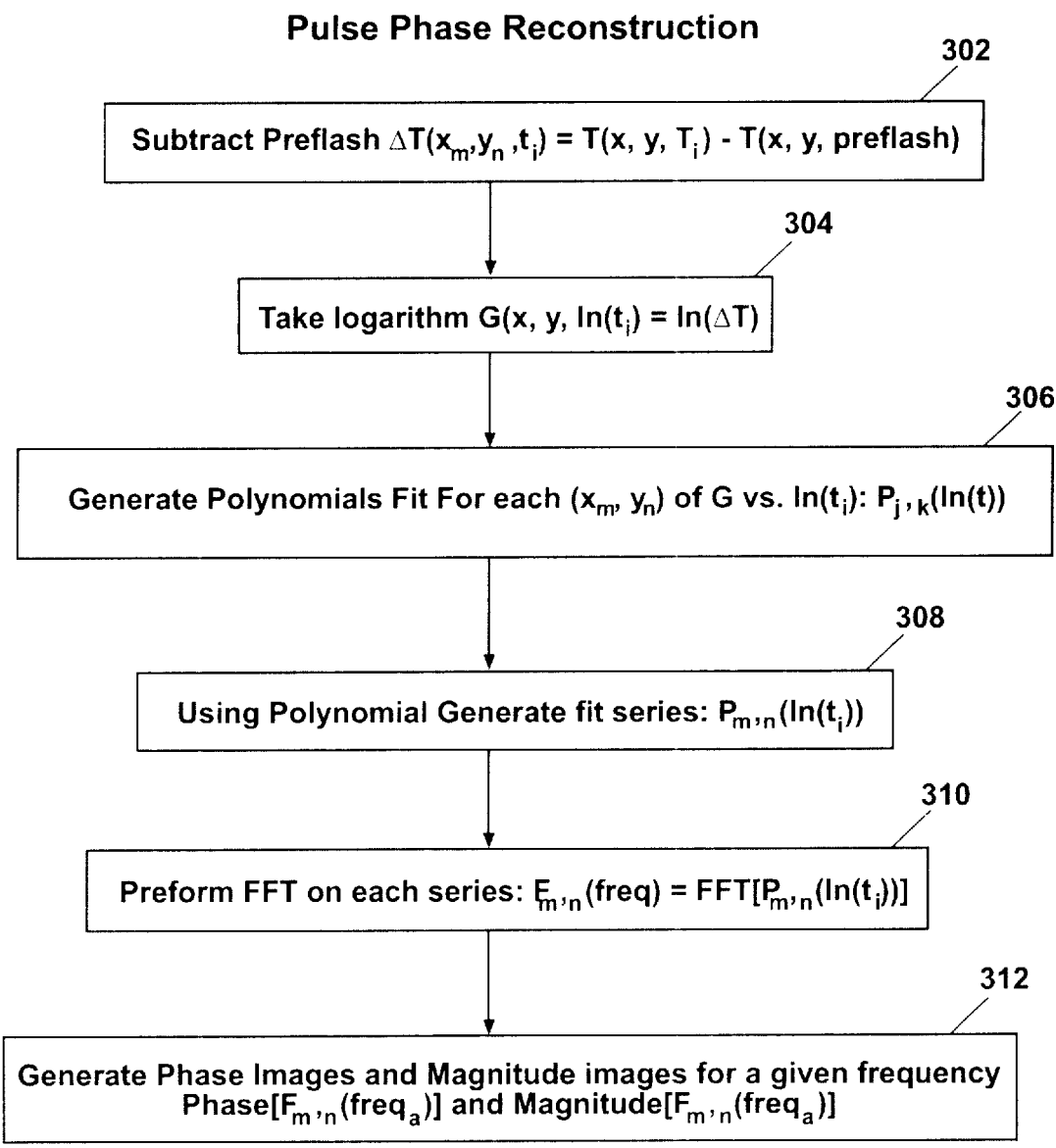
FIG. 13 is a flow chart of the present invention as it applies to generating a reconstructed defect map using pulse phase information.

The flowchart of FIG. 13 shows how the polynomial reconstruction of the present invention can be easily applied to pulse phase thermography. Pulse phase thermography is a well known technique wherein a thermographic image is constructed from a pulse phase image and a pulse magnitude image. The first four steps (steps 302–308) of FIG. 13 closely track steps 210–222 of FIG. 2.

However, in the reconstructed pulse phase method, a Fast Fourier Transform (FFT) is performed on I(t), the reconstructed time history of each pixel, so that the result is complex, with a real and imaginary component, i.e. F[I(t)]= Re{F[I(t)]}+i Im{F[I(t)]}

The real and imaginary components are used to generate a phase or magnitude image, based on the relationship
Phase=arctan(-Im{F[I(t)]}/Re{F[I(t)]})

and Amplitude=sqrt (F[I(t)]F*[I(t)])

where F* is the complex conjugate of the FFT.

Since the FFT of the time history is a function of frequency, rather than time, the phase varies with frequency. It is particularly useful to find the maximum phase value for each pixel, and create a maximum phase image, as this provide a map of subsurface defects, which are typically out of phase with defect free areas. However, the presence of noise in the signal typically makes discrimination of maximum phase difficult for all but very shallow or gross defects.

Figure 14:
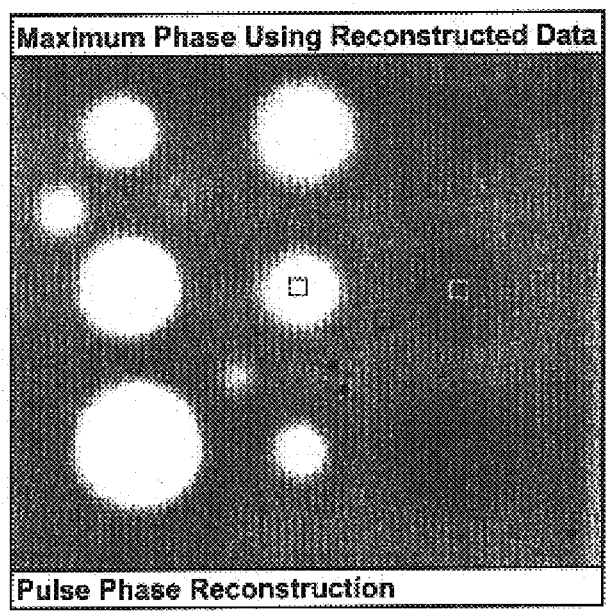
FIG. 14 is a reconstructed defect map image fabricated by using pulse phase thermography techniques in conjunction with the data reconstruction technique of FIG. 2.
Figure 15:
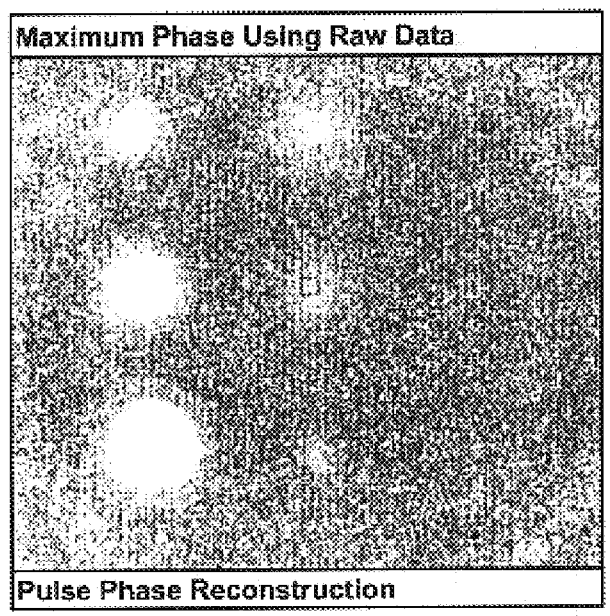
FIG. 15 is a defect map constructed using pulse phase thermography and raw data (i.e. data that has not been reconstructed using the present invention).

FIG. 14 is a phase image created from reconstructed data. This stands in stark contrast to the image of FIG. 15 which is a phase image constructed from raw data. The reason why the reconstructed phase image of FIG. 14 is vastly superior to that of FIG. 15 is that whenever FFT's are involved in data manipulation, they are very sensitive to noise. Because the reconstructed method of the present invention eliminates most, if not all, of the noise from the data, the end result is vastly superior to that which is achievable using traditional pulse phase techniques in conjunction with raw data.

Multiple Polynomials

Although the above examples focus on using a single polynomial expression as the reconstructed function to describe the temperature-time characteristic for a given sample, more than one polynomial expression may be desired to address the thermal behavior at the extremes of the temperature time characteristic and prevent the extremes from skewing the analysis of the temperature-time behavior of the sample. More particularly, with reference to FIG. 16, the polynomial fit when using one polynomial may be adversely affected by the temperature-time curve behavior at the very early and very late stages. As noted above, in the early stages immediately after flash heating, the infrared camera data may become briefly saturated and may initially display non-linear behavior that does not reflect the thermal characteristics of the sample accurately. In the late stages, the temperature-time characteristic of the sample tends to be weaker and therefore more susceptible to noise and/or temperature fluctuations due to convection or stray radiation.

Figure 16:
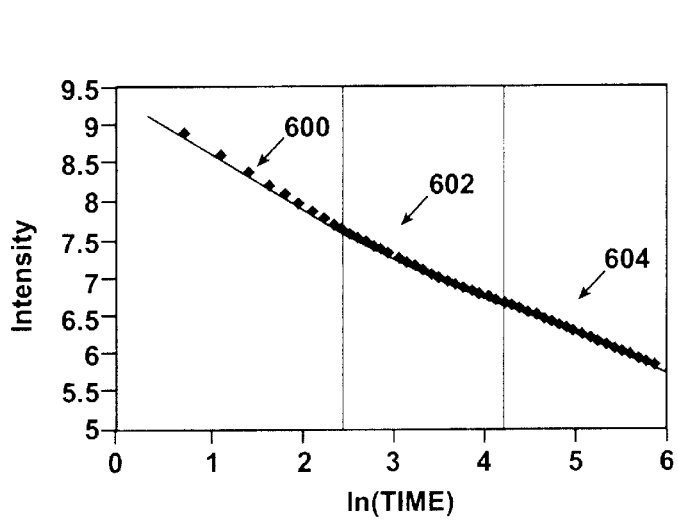
FIG. 16 is a graph illustrating how the present system can be used to fit two or more polynomials to image data.

To prevent the extreme portions of the temperature-time characteristic from influencing the results in the central region, the example shown in FIG. 16 uses more than one polynomial equation to describe the complete temperature-time history of each pixel. In the example shown in FIG. 16, the temperature-time characteristic is divided into early, intermediate, and late behavior regions, 600, 602 and 604 respectively, each of which exhibit slightly different temporal behavior, and each region is described using a different low-order polynomial. When viewed separately, the temperature-time characteristic for each individual region 600, 602, 604 behaves more like a linear function than a single plot of the entire time sequence. As a result, each separate region is more easily approximated by a low-order polynomial than the entire temperature-time plot.

Detecting defects using the polynomial for each region is the same as described above. More particularly, the processor can calculate first, second, or higher derivatives of one or more of the polynomials. Further, as explained above, the zero crossing behavior of the second derivative can be used to determine the depth of a defect. Note that the defect depth can also be determined by finding the point in time at which the first derivative of the polynomial representing the reconstructed function deviates from −0.5 by a predetermined threshold. The −0.5 value is generated based on the known temperature characteristic of a semi-infinite solid that has been instantaneously flash-heated, which can be described as:

$$T = \frac{Q}{e(\pi t)^{1/2}} \tag{7}$$

where T is the temperature change relative to the initial temperature, e is the thermal effusivity of the material (the square root of the product of the density, thermal conductivity and heat capacity), Q is the energy input to the sample by the flash-heating, and t is the elapsed time after flash-heating. When the natural logarithm of the equation is taken, the resulting expression is:

$$\ln(T)=(Q/e\pi)-0.5\ln(t) \tag{8}$$

As can be seen in the above equation, the natural logarithm of the temperature-time data includes a time-dependent term with a slope of −0.5 that is independent of material properties.

During sample evaluation, the above two equations are useful because a sample will behave like a semi-infinite sample, such that the natural logarithm of the temperature-time data has a slope of −0.5, as heat propagates from the surface into the bulk of the sample until a defect or boundary is encountered. If there is a defect or boundary in the sample, the temperature-time data will deviate from the −0.5 slope. As a result, the first derivative expression can be used to detect defects by checking whether the first derivative for a given pixel deviates from −0.5 based on this equation.

Mosaic

Note that for a larger sample, the camera's field of view is often impracticable to acquire an image of the entire sample in one image frame. In such applications, in order to create integrated subsurface image of the entire sample, the individual portions must be assembled together to form a complete image (or mosaic). Presently this is done manually or using a graphics program. Problems may occur, however, because creating the complete image using conventional raw image data can be time-consuming and may be much slower than the rate at which image data is acquired. Furthermore, temperature variations due to varying input energy temperature and camera settings complicate exact matching of any images of adjacent portions.

Figure 17:
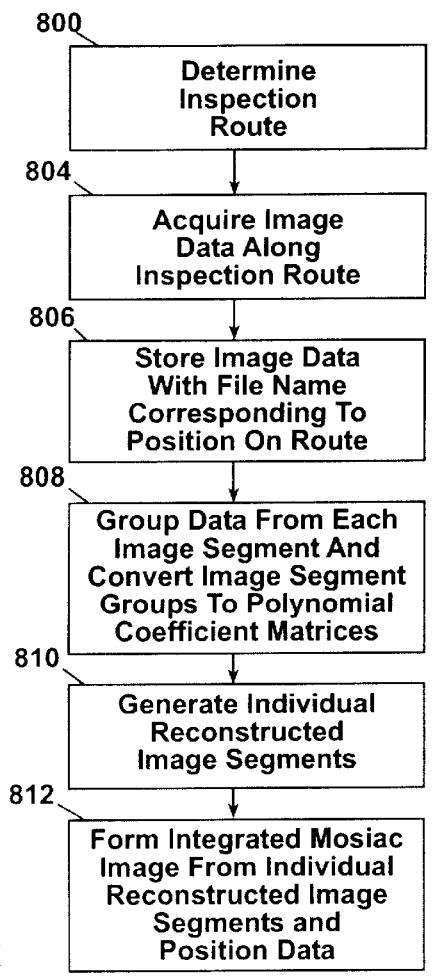
FIG. 17 is a flowchart illustrating one embodiment of the disclosed invention and its application to integrating two or more image segments.
Figure 18:
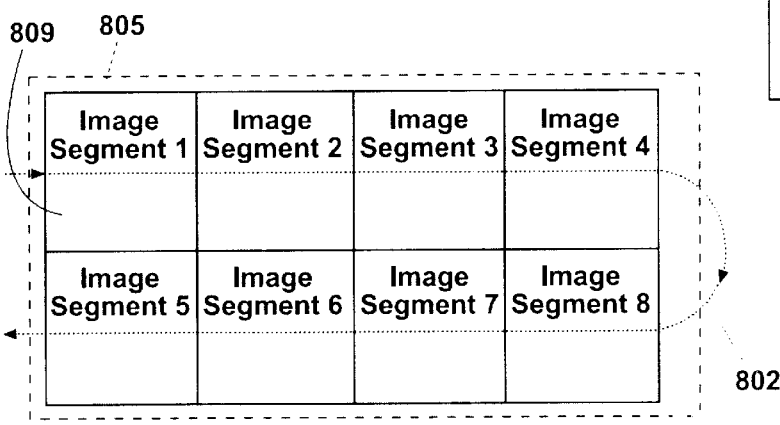
FIG. 18 is a representative diagram of an integrated mosaic image generated according to the method shown in FIG. 17.

FIG. 17 is a flowchart illustrating one way in which the inventive system can handle samples requiring multiple segments to cover its entire surface without encountering time delay problems caused by managing raw data. First, before the actual inspection process occurs, an inspector determines the route that will be used to cover the inspection area at step 800. As illustrated in FIG. 18, the inspection route 802 involves obtaining image data while moving along a path from, for example, left to right in rows, or alternating left-right and right-left rows, or columns, etc.

Next, the image data for each frame is acquired and stored at step 804. Each frame within each image segment is stored along with time and position indexes associated therewith. The time and position indexes corresponding to the frame's time sequence and spatial position in the inspection route at step 806, allow sequential frames to be correctly ordered at a later time. Note that this time sequencing does not have to be measured on an absolute time scale (although it can be measured as such). It can be measured in terms of relative start time (time elapsing since the first frame in the current image segment), or it can also be measured in terms of frame sequence (if the frame rate is stable, frame sequence is simply measured in the sequence of raw frames—i.e. frame 1, frame 2, . . . frame n).

The image data from each image segment is grouped together and converted from its raw digital format to a matrix of polynomial coefficients in the manner described above at step 808. The conversion step 808 can be conducted for each sample segment (i.e. position) as the acquisition each image segment is complete (but prior to collecting data for the next image segment). Alternatively, the data from all of the frames of all of the image segments can be acquired and stored in the raw digital format for later conversion.

Once the raw digital data for all of the frames has been converted into polynomial coefficient matrices at step 808, a reconstructed image for each image segment 809, which is generated from the coefficient matrices can be placed automatically in the appropriate position at step 812 based on each image segment position in the inspection route 802. In other words, the reconstructed mosaic comprised of multiple image segments is assembled using the spatial information from step 806 to position each image segment and to form a completed single mosaic image to be displayed at step 810. An example of a mosaic 805 image is shown in FIG. 18.

The system can provide the user with the option to select a particular display mode (e.g. reconstructed image, $1^{st}$ or $2^{nd}$ or $3^{rd}$ or higher derivatives, reconstructed pulse phase image derivative, or depth map) through a user interface (not shown) such as a computer keyboard. The maximum number of images that can be loaded into the program depends on the amount of RAM available to the program. The mosaic image will have the same image characteristics as single image sequences and can be updated quickly as the user views images over time or conducts mathematical operations on the image data. More particularly, any changes in successive images or mathematically manipulated images can be generated nearly instantaneously because the invention manipulates reconstructed data (the polynomial coefficients) and not the raw data, simplifying the calculation process.

As a result, the inventive system and method generates a data structure, which is based on the original data sequence obtained from the infrared camera, that is more compact, easier to manipulate mathematically, and less prone to temporal noise than the original data sequence but that still preserves the characteristics that indicate the presence of sub-surface defects. By reducing temporal noise, the inventive system allows the inventive system to provide a significant signal to noise improvement allowing relatively inexpensive infrared cameras (e.g. uncooled microbolometer cameras such as the Indigo Systems Alpha™ which are available at a fraction of the cost of high performance cameras) to be used. Furthermore, because the data structure generated by the invention is much smaller than the image data structure obtained from the camera, the stored data can be differentiated and integrated with respect to time more easily than the original data generated by the camera. The analysis and manipulation of the data from the camera can be conducted in an automated fashion, without any user intervention or adjustment. Assembling a total image mosaic from individual image frames according to the invention allows large structures to be inspected quickly using equipment that covers a smaller field of view than the structure's entire area. This advantage applies to viewing microscopic images also, where regions of the microscopic subject must be assembled into a composite. Thus, the mosaic capability of the present application not only extends to macroscopic applications but extends to microscopic applications as well. Unlike graphics programs, the mosaic method of the present invention is capable of manipulating an entire data image as a single entity.

The inventive system can be used alone or as a pre-processing step in conjunction with other methods for measuring, characterizing, and/or recognizing defects or sample material properties. Although the above-described configuration uses an infrared camera to acquire the data and transfers the data to a computer for further processing, the entire system can be incorporated into the camera itself without a separate computer. Also, although the above example analyzes infrared image data, the inventive system and method can be applied to any data set that is in response to a stimulus that causes a monotonically increasing or decreasing response and where there is no random motion in the field of view in which the data is generated.

Vibrothermography

Vibrothermography was first developed in the late 1970s and early 1980s as a means for nondestructively characterizing and evaluating solid materials. The method was used to identify cracks and subsurface anomalies such as disbonds and delaminations in metals, ceramics, and composite materials. Now referring to FIG. 19, the basic technique involves generating acoustic energy in the range of 10 kHz to 30 kHz and applying that energy (either continuously or in a time varying mode) to a sample 902. The acoustic energy is absorbed by the sample which causes internal frictional heating between the faces of the crack or disbond 904. This internal heating results in a transient local temperature rise 903 on the surface of the sample near the anomaly. This local temperature rise can be detected using an infrared camera 906. The acoustic energy is created by a ultrasonic transducer 910 which is powered by ultrasonic transducer power supply 900.

Although vibrothermography enjoys application in some niche markets, it has several shortcomings which prevent its widespread use. Some of those shortcomings are as follows:

A. In practice, the ultrasonic transducers used to excite the sample are high powered devices (1 kW or greater), typically designed for ultrasonic welding applications. Such high levels of ultrasonic energy pose a safety hazard to inspectors in the vicinity of the inspection station, and often the ultrasonic energy causes damage to surface of the sample. Moreover, the tendency of practitioners of vibrothermography tend to be moving to even higher powered devices as more challenging applications are confronted.

B. The interpretation of the thermographic results generated from the vibrothermography technique are almost entirely visual, making automation of the inspection process difficult, if not impossible.

C. The interaction and reflection between the sample (including sample edges and sample structural elements) and the acoustic/elastic waves, gives rise to mode patterns that manifest themselves in misleading image artifacts.

The application of the reconstruction method set forth in FIG. 2 to vibrothermography gives rise to 3 important advantages which are not available using traditional vibrothermography systems. Specifically:

A. it allows cracks and subsurface defects to be detected using much lower power acoustic or ultrasonic energy than is used in traditional vibrothermography applications.

B. it allows complete automation of the defect detection process.

Figure 19:
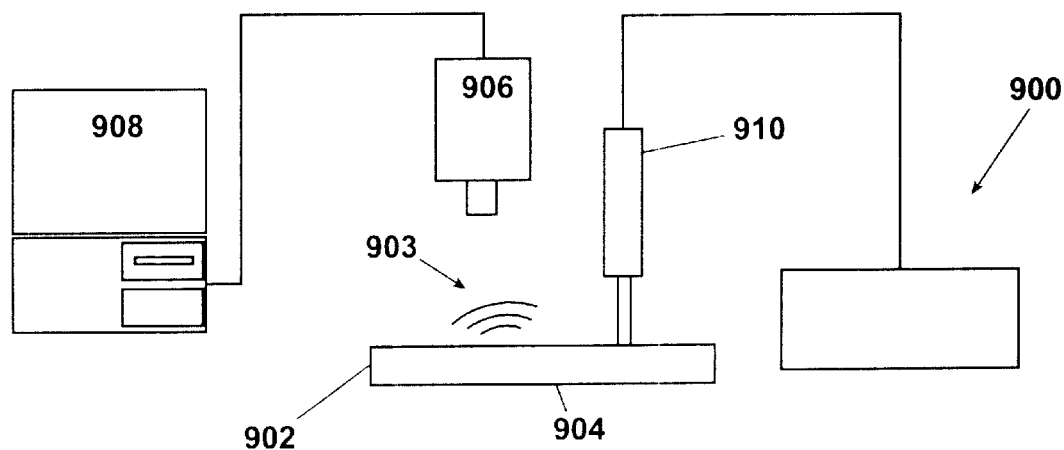
FIG. 19 is a schematic depiction of the hardware embodiment of the present invention used to implement a vibrothermography application.

C. it removes image artifacts due to mode conversion or interference effects which are inherently present using vibrothermography. This vibrothermography application of the present invention uses traditional vibrothermography hardware (as seen in FIG. 19).

However, the novel signal processing approach as set forth in FIGS. 2 et seq. provide the improvements set forth above.

Figure 20:
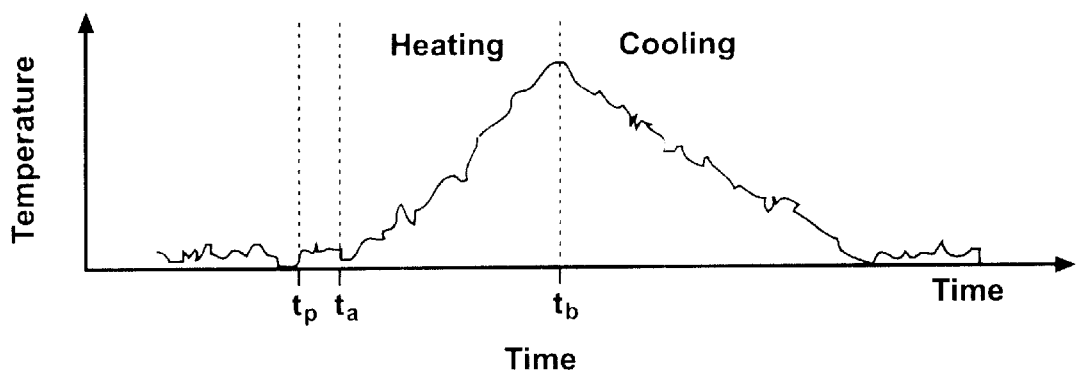
FIG. 20 is a temperature-time graph of a portion of sample 102 of FIG. 19 which receives acoustic energy.

Now referring to FIG. 20, during time interval $t_a<T<t_b$ when the acoustic excitation is applied, the temperature of the sample rises monotonically. After $t_b$ (when the acoustic energy is no longer imparted to the sample), the temperature of the sample is at an exponential rate in the same manner as we have already discussed in conjunction with FIG. 3A. When this temperature signature is captured by infrared camera 106, the resulting data generated therefrom is corrupted by temporal noise from the infrared camera electronics. This noise becomes more significant as the amplitude of the thermal signature decays (hence the trend in vibrothermography toward higher power excitation sources). When an image is constructed, comprising an array of pixels whose noise behavior is similar to, but uncorrelated with, the above example, the net result is an image which is corrupted with significant spatial noise. This noise can easily obscure, or completely mask, the very sample defects that it is designed to detect. However, by applying the data reconstruction techniques which have already been discussed in conjunction with FIG. 2 et seq., the noise corruption inherent in the captured data is largely eliminated.

Still another approach to vibrothermography is to use the data reconstruction technique set forth in FIG. 2 et seq. in conjunction with the pulse phase approach discussed earlier. Although the concept of pulse phase thermography is well known in the context of optically excited pulsed thermography, it has not been possible (until now) to apply it to vibrothermography because the high frequency noise dominates the signal and conventional averaging techniques used to reduce the noise also reduce the signal. Since the reconstruction techniques introduced herein reduce the noise but not the signal, they are ideally suited for application to pulsed phase vibrothermography. In this embodiment, we take the discrete Fourier transform of the polynomial expression for each pixel, and use the resulting real and imaginary parts of the results to create either a magnitude or a phase image. This approach has already been discussed in detail in conjunction with FIGS. 13–15. This approach serves to increase the sensitivity of the vibrothermography technique by reducing temporal (and consequently) spatial noise and by further emphasizing weak signals through the use of derivative images. The reconstructed data created by the polynomials also allows the detection process to be automated. This can be done by finding influction points in the first, second or third derivatives as has already been discussed in conjunction with FIGS. 9A–9E.

After performing the steps described above, the resulting images would be essentially free of high frequency temporal noise. Artifacts due to acoustic wave mode effects may remain; however, these are easily removed because they have slower rise times and different time-derivative behavior than actual cracks. The process of viewing the infrared "movie" of the excitation can be eliminated by calculating the integral of the polynomial representation of the surface temperature for each pixel over the duration of the heating period. Since frictional heating will only occur in those areas where cracks or subsurface defects occur, the integral of a defect free point will be small compared to a point near a crack (regardless of whether that crack is a surface crack or a subsurface crack). However, integration of the noise-reduced reconstruction data allows detection of more subtle features and the use of lower excitation energy than simple addition schemes which employ noisy data.

The final result is a sequence of images of cracks or subsurface features that offers far more detail than current vibrothermography techniques allow. The increased sensitivity of detection due to the processing scheme disclosed herein allows the use of far less excitation energy (approximately 50% or less) than currently use "brute force" methods such as those described in the introduction.

Scanning Thermography

In pulsed thermography, a portion of a solid sample is heated with a brief energy pulse (using like energy, hot air, ultrasonic energy, or any other pulse means), and the transient temperature response of the sheeted portion of the sample is measured using an infrared camera. The data from the camera is used to generate an image of the subsurface structure of the targeted portion of the sample. The method is fast (approximately 10 seconds per square foot), does not require contact with (or immersion of) the sample, and does not use ionizing radiation. Portable systems optimized for use in the field, are available commercially and recent advances have resulted in tremendous improvements in the ability of pulse systems to perform precise depth or thickness measurements. However, despite the many attractive advantages of pulsed thermography, there are some fundamental obstacles that limit wider implementation. This is particularly true in cases where there is a need to evaluate very thick or very thin structures. Some of these obstacles include the following:

A. Post-flash saturation: for many applications, particularly detection and measurement of corrosion, it is essential to measure the thermal response of the test area immediately after flash heating is applied. Unfortunately, as much as 30 millisec of this early-time data is often lost because the energy from the flash is reflected from the sample surface causing the detectors in the infrared camera to saturate. If the flash energy is reduced to compensate, the sensitivity of the system is reduced proportionately.

B. Scan advantage: the lamps used in scanned systems operate continuously and deliver a constant power output (rather than the high peak energy output that gives rise to saturation in pulsed thermography systems). Furthermore, the primary source of saturation is the flash energy reflected off of the sample surface. Since the scanned lamp passed over the target area prior to the camera passing over the same target area, it is possible to shield the camera from the direct lamp reflection in a scanned system, thus minimizing the possibility of detector saturation.

C. Input power/depth limitations: pulse thermography has been most effective on relatively thin structures (e.g. for metal aircraft skins approximately less than 0.050 inches, for composite materials approximately less than 8 plies). For many structures where skin thickness may exceed 0.100 inches, pulse thermography is only capable of detecting relatively large defects. As input power is increased in order to increase sensitivity toward accommodating thicker structures, the saturation problem is exacerbated, and the size of the thermal imaging unit becomes impractical for use in the field.

D. Scan advantage: it is relatively simple to control the amount of energy delivered to a sample by a scanning system by simply adjusting the scan speed and/or the lamp aperture size (the portion of the lamp that is exposed to the surface). A large amount of energy can be deposited using inexpensive halogen lamps housed in a small reflector.

E. Optimization for inspection of large structures: for inspection of large structures (e.g. control surfaces, radomes, fuselage or masts), pulsed thermography requires that the inspection unit remain stationary over the target area for a fixed interval of time (typically 5 to 10 seconds) before it is moved to the next portion of the sample to be imaged. A typical inspection may generate hundreds of image files, which can be stitched together into a single mosaic image after the entire area has been scanned. The start/stop acquisition process requires the use of markers or similar means to be placed on the part. This complicates implementation using a robot or a creeper.

F. Scan advantage: scanning systems are ideal for continuous operation on large structures.

Despite the above referenced advantages, scanning thermography systems are qualitative, depend highly on the operator's experience and training, and tend to have poor spatial resolution compared to pulsed systems. Additionally, when imaging large structures, the amount of data acquired, can be prohibitively large. In addition, the precise control of the velocity of the camera or the sample must be maintained. The scanning embodiment of the present invention combines the strength of pulse in scanned thermography to detect and characterize deeper defects and more massive structures than were heretofore possible using traditional scanned thermography techniques. Using the enhanced scanning system of the present invention, large scale structures can be inspected quickly and relatively inexpensively. This improvement is made possible by the present invention because of the significant signal to noise improvement and data compression that is made possible by applying the signal processing methods disclosed in conjunction with FIG. 2 et seq. The scanning embodiment disclosed herein can be implemented in a fully automated fashion and applied to thick or massive composite structures (e.g. spars and pressure vessels)—structures that are currently beyond the capability of pulsed systems. It can also be applied to thin, reflective structures (e.g. aluminum alloy aircraft skins) that are not particularly well suited for examination by existing scanning systems. The present scanning embodiment of the present invention extends the state of the art beyond the capabilities of existing pulsed or scanned systems.

Figure 21:
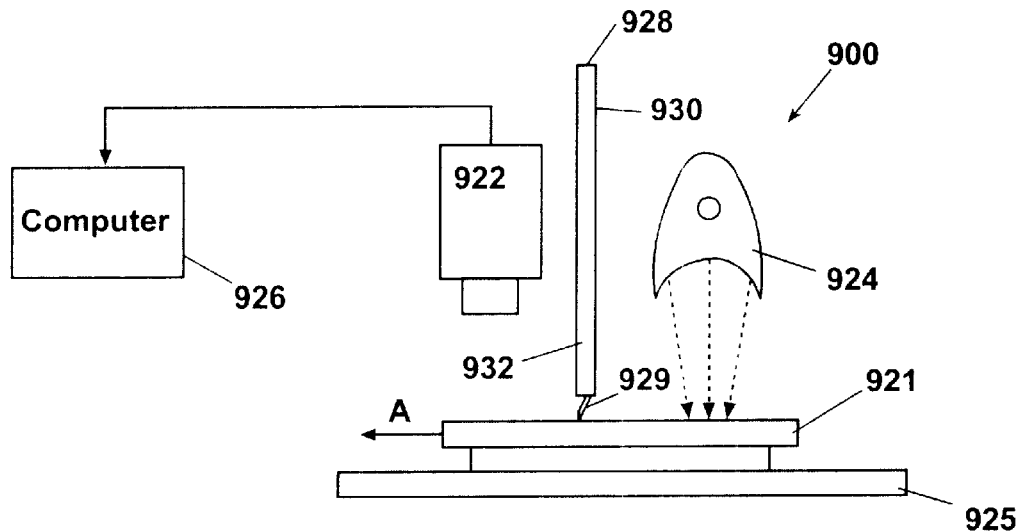
FIG. 21 is a schematic depiction of a hardware embodiment of the present invention used to implement a scanned thermography application of the present invention (using a moving sample and fixed camera arrangement).
Figure 22:
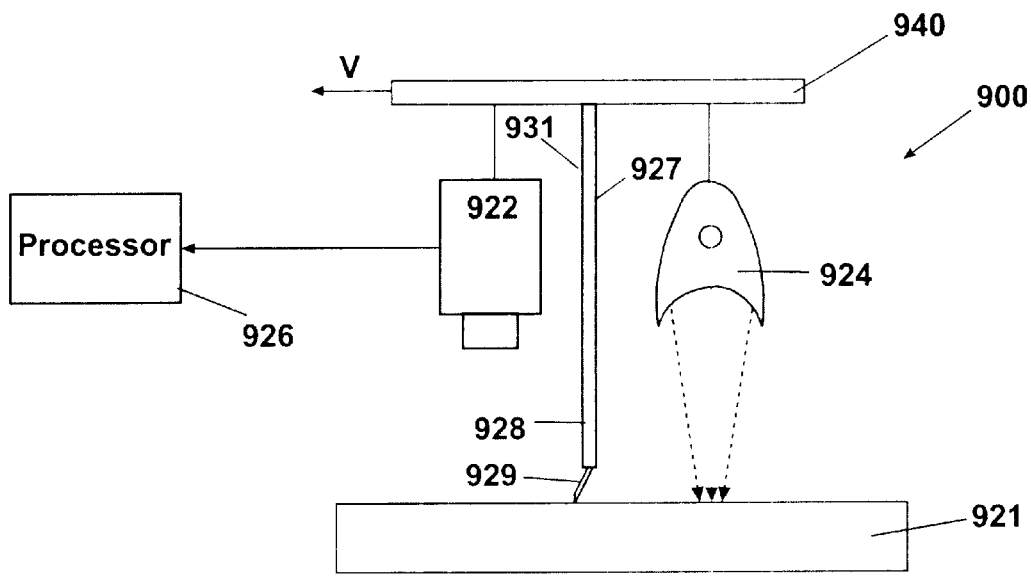
FIG. 22 is a schematic depiction of the hardware embodiment of the present invention used to implement a scanned thermography application of the present invention (using movable camera and stationary sample arrangement).

Now referring to FIG. 21, heat source 924 is used to continually heat sample 921 as sample is carried along direction A by translator (or conveyor belt 925 ). Heat source 924 can be comprised of any number of heating devices including, but not limited to, a quartz halogen lamp, a hot wire, ultrasonic energy, hot air, or hot water. Translator 925 is used to move the sample past heat source 924. In the embodiment set out in FIG. 22, instead of moving the sample 921 past the heat source 924, the heat source 924 is moved past the stationary sample 921. Each technique has advantages and disadvantages over the other technique and the most appropriate technique is largely determined by the environment in which the samples are to be tested and the size of the sample. In both embodiments, there is a fixed distance between camera 922 and light source 924 and there is, in both embodiments, relative motion between light source 924 and sample 921. Computer 926 is equipped with a digital or analogue frame grabber capable of acquiring continuous image data from camera 922. Camera 922 and heat source 924 are separated by shield 928. Shield 928 can optionally be fitted with gasket 929 to prevent excessive leakage of infrared energy from source 924 into the field of view of camera 922. The side surface 927 of shield 928 which is closest to heat source 924 can be optionally coated or otherwise be made reflective to minimize heating of the shield 928. Side 931 of shield 928 which faces camera 922 can be optionally coated with, or otherwise be made to have a low infrared emissivity to minimize emission into the field of view of camera 922. In normal operation, there is relative movement (of a constant velocity) between sample 921 and camera/heater pair 922/924. While this relative movement of constant velocity takes place, heater 924 projects a line of light onto sample 921 and the camera acquires a sequential image of the heated area after it passes shield 928.

Figure 23:
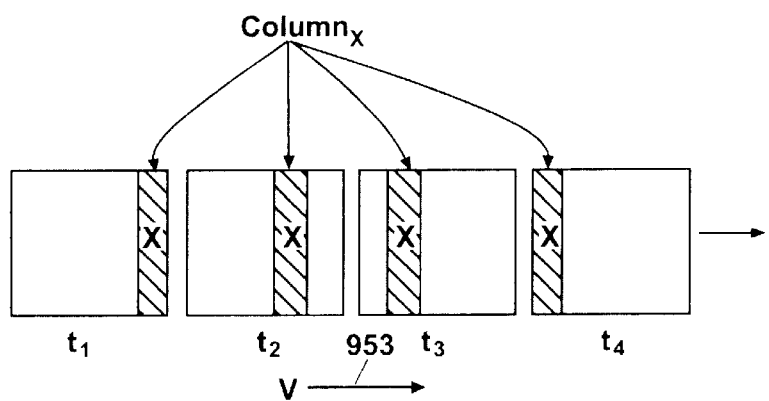
FIG. 23 is a depiction of a sequence of images frames captured by a scanning application of the present invention.
Figure 24:
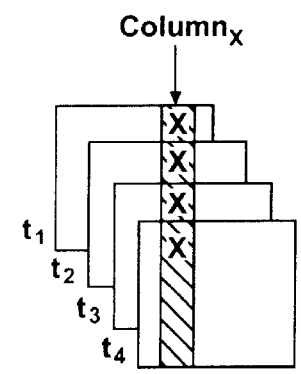
FIG. 24 is a depiction of the digital manipulation of images captured in FIG. 23 in order to generate the temperature-time history of an image segment according to the reconstruction technique of the present invention.

Once the infrared signature is captured by camera 922 and converted into an electronic data format, it is transferred to computer 926 where it is processed. Within computer 926, the data undergoes a sequence of steps to spatially rearrange it into a coherent image, remove scanning and illumination artifacts, and enhance subsurface features in the data. The first step is a relatively simple "bookkeeping" task in which the incoming scanned data (FIG. 23) is rearranged into "data cubes" (i.e. a collection of spatially stationary temperature-time plot representing each pixel in the field of view, see FIG. 24). As the camera captures the thermal images from the sample, image columns (shown as $Column_x$ in FIG. 23) perpendicular to the direction of motion 953 are organized such that each Column x in the datacube represents a common portion of the sample surface at progressively later times after this sample has been heated. This process is graphically depicted in FIGS. 23 and 24 wherein a series of four images is scanned with a horizontal velocity v and they are thereafter arranged so that the x (which represents a fixed location on the surface of the object to be sampled) appears to be stationary.

After spatial rearrangement of the data into a datacube (which represents the temperature-time history for each portion of the sample which has been imaged), the data is transformed using the method set forth in FIG. 2, steps 212 through 227. All of the benefits provided by the reconstruction method of the present invention, apply equally to this scanning embodiment. The reconstruction method of the present invention is particularly beneficial for the scanning embodiment because of the massive amounts of data which are generated from long, continuous samples (long continuous samples are particularly well suited for imaging using the scanning embodiment). It is not unusual in a typical scanning application to generate several hundred frames of data, each frame containing thousands of pixels. Because the reconstruction technique of the present invention works with coefficients of polynomials (and not the raw data itself) only the coefficients need to be stored, manipulated, and displayed regardless of the length of the original raw data sequence. The present invention can easily reduce a 50 MB (megabyte) datacube of the image sequence to 4.5 MB.

Characterizing and Comparing Thermal Image Data Sequence Using TSR

Numerous methods have been proposed and developed for nondestructive inspection using active thermography.

These methods often involve creating an infrared image, or an image sequence, of a sample after it has been thermally excited, and comparing the resulting image or sequence with that of a previously characterized reference sample. However, in practice comparison of either single images or image sequences is complicated by the need for exact alignment of the samples. Additionally, the comparison is also made difficult because of variations between images caused by variation of excitation energy, camera calibration, and ambient temperature etc.

The TSR method (as already explained in conjunction with FIG. 2 et seq.) permits fast calculation of derivatives (with respect to ln(time)) of the logarithmic temperature-time history of each pixel. The resulting derivative is extremely accurate because it is based on the noise-reduced TSR signal. We can use these benefits to exploit the highly deterministic nature of the logarithmic temperature-time behavior, and quantitatively and efficiently characterize and compare entire thermographic data sequences, rather than single images. Our approach is immune to the factors described above, and does not require a human operator to compare or evaluate results.

Figure 25A:
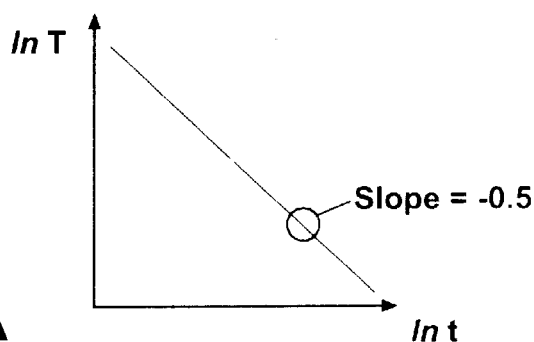
FIG. 25A is a time/temperature graphical representation of a one-dimensional heat flow equation.
Figure 25B:
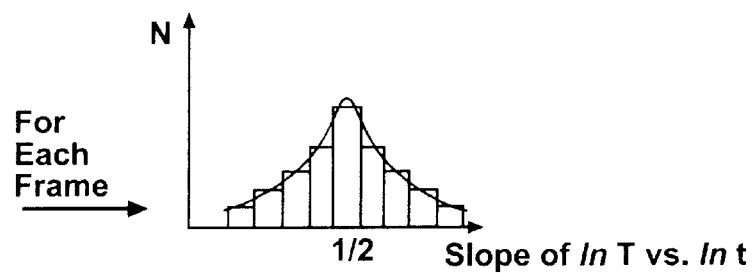
FIG. 25B is a histogram depicting the time derivative of every frame in the sequence of FIG. 25A.
Figure 25C:
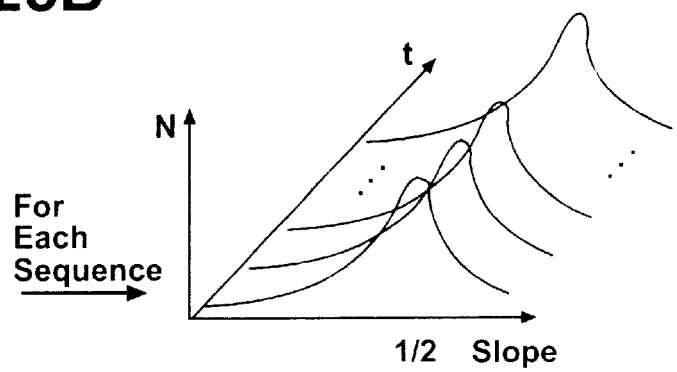
FIG. 25C is a set of histograms collected over time.
Figure 25D:
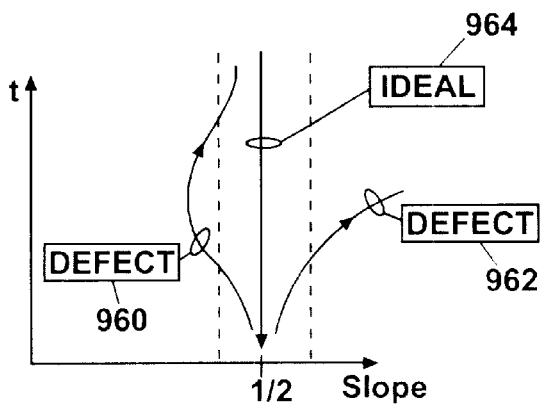
FIG. 25D is a top view of one ideal sequence of histograms and two defective sequences of histograms.

From the solution to the 1-dimensional heat flow equation for a semi-infinite sample that is uniformly heated at the surface by an instantaneous pulse, we know that the slope (with respect to ln(t)) of the logarithmic temperature-time sequence is −0.5 (see FIG. 25A). This fact is independent of the material composition of the sample or the camera used to acquire the data, and remains true until a subsurface boundary (i.e. a defect or a wall) is encountered. Thus, we create a histogram (number of pixels vs. ln (T)/ln (t)) for the time derivative of every frame in the sequence (see FIG. 25B). For a defect free sample, the histogram will be sharply peaked about −0.5. If we consider the top down view of the entire set of these histograms (see FIG. 25C), we will see a relatively straight line that follows a constant slope of −0.5 (see FIG. 25D). However, if a defect is encountered, a branch deviation 960, 962 from the ideal line 964 will emerge at a time that is proportional to the depth of that defect. The net result of this approach is that it reduces the behavior of the entire data sequence to a single image, or even a single curve if we just consider the primary and secondary peaks of the histogram. As subsequent acquisitions occur, they can be compared to a master image of the histogram sequence projection (e.g. the master can be subtracted from subsequent results with the expectation that the result should be a nearly null image for a defect free sample). It is important to note that this approach does not depend on precise pixel to pixel registration between samples, or exact replication of excitation energy levels or ambient conditions, as it utilizes the logarithmic slope behavior, which is highly deterministic.

It should be understood that various alternatives to the embodiments of the invention described herein may be employed in practicing the invention. It is intended that the following claims define the scope of the invention and that the method and apparatus within the scope of these claims and their equivalents be covered thereby.

What is claimed is:

1. A system for determining a time response to a monotonically changing characteristic of a sample, comprising:
   a camera that obtains at least two different images of the sample over time, each image having a plurality of pixels, each pixel having an amplitude corresponding to the monotonically changing characteristic of the sample;
   a controller coupled to at least one of the sample or the camera for moving the camera or the sample spatially to obtain said at least two different images of the sample; and
   a processor that receives the plurality of images and generates a data array for each of the spatially different images, the data array corresponding to a logarithm of the pixel amplitude at a given time and a logarithm of the given time,
   wherein the processor fits a polynomial representing a reconstructed function to at least a portion of the data array, the polynomial having at least one polynomial coefficient, such that each pixel in said different images is represented by a coefficient array containing said at least one polynomial coefficient, and
   wherein the processor generates from coefficient arrays at least two reconstructed images corresponding to said at least two different images.

2. The system of claim 1, wherein the two different images are spatially different images separated from one another along a pre-determined inspection route and wherein said processor forms an image mosaic from the reconstructed images.

3. The system of claim 2, wherein the processor includes an acquisition module that generates time and date for information stamp data for each of the spatially different images based on each image's position on the inspection route, and wherein the stamp data is used to position each of said reconstructed images in the image mosaic.

4. The system of claim 3, wherein the stamp data is at least one of time and data information or position data.

5. The system of claim 1, wherein the processor generates the coefficient array for each pixel in each of said different images as each image is obtained by the camera.

6. The system of claim 1, wherein the processor obtains said at least two of different images before generating the coefficient array for each of the different images.

7. The system of claim 1, wherein the logarithm of the pixel amplitude or the logarithm of the given time includes applying a natural logarithm or scaling using a $T^{-2}$ factor where T=time.

8. The system of claim 1, wherein the processor calculates a first derivative of the reconstructed function for a specified time value.

9. The system of claim 8, wherein the processor determines whether the first derivative of the reconstructed function for each pixel over time deviates from −0.5 by a predetermined threshold.

10. The system of claim 8, wherein the processor calculates a second derivative of the reconstructed function for a specified time value.

11. The system of claim 10, wherein the processor determines whether the second derivative of the reconstructed function for each pixel has a zero crossing, wherein the presence of the zero crossing indicates a defective pixel and the absence of the zero crossing indicates a defect-free pixel.

12. The system of claim 11, wherein the processor converts the logarithm of the earliest zero crossing time of the second derivative of the reconstructed function into a linear time domain for defective pixels, assigning a reserved value for defect-free pixels, and using the reserved value and the converted zero crossing time for each pixel to generate a defect map array that uses a first color value for defective pixels and a second color value for defect-free pixels.

13. The system of claim 1, wherein the processor generates a reference polynomial and subtracts the reconstructed function from the reference polynomial to generate a contrast curve, wherein a peak in the contrast curve indicates the presence of a subsurface defect.

14. The system of claim 1, wherein the processor fits a first polynomial to a first portion of the data array and a second polynomial to a second portion of the data array to generate the reconstructed function.

15. The system of claim 1, wherein the processor divides the data array into an early region, an intermediate region, and a late region and fits a first polynomial to the early region, a second polynomial to the intermediate region, and a third polynomial to the late region to generate the reconstructed function.

16. The system of claim 1, further comprising a memory that stores said coefficient array.

17. The system of claim 16, wherein the coefficient array is stored in the memory as a file having a size that is independent of the number of images obtained by the camera.

18. A method for determining a time response to a monotonic change in a characteristic of a sample, comprising the acts of:

obtaining a plurality of different images of the sample over time, each different image having a plurality of pixels each having an amplitude corresponding to the monotonically changing characteristic of the sample;

generating a data array for each of the plurality of pixels, the data array corresponding to the logarithm of the pixel amplitude at a given time and the logarithm of the given time;

fitting a polynomial representing a reconstructed function to the data array associated with at least a portion of the plurality of pixels, the polynomial having at least two polynomial coefficients, such that each pixel in said portion of plurality of pixels is represented by a coefficient array containing said at least two polynomial coefficients;

generating a plurality of reconstructed images corresponding to the plurality of different images.

19. The method of claim 18, wherein the obtaining different images step includes the step of obtaining spatially different images along a pre-determined inspection route.

20. The method of claim 18, further comprising the act of generating stamp data for each of the spatially different images based on each image's position on the inspection route, wherein the forming act uses the stamp data to position the reconstructed images in the image mosaic.

21. The system of claim 20, wherein the stamp data is at least one of time and data information or position data.

22. The method of claim 18, wherein the fitting act generates the coefficient array for each pixel in each of said different images as each image is obtained.

23. The method of claim 18, wherein the obtaining act obtains a plurality of the different images before the fitting act generates the coefficient array for each of the different images.

24. The method of claim 18, further comprising the act of calculating an instantaneous first derivative of the reconstructed function for a specified time value.

25. The method of claim 24, further comprising the act of determining whether the first derivative of the reconstructed function for each pixel over time deviates from a slope of −0.5.

26. The method of claim 24, further comprising the act of calculating an instantaneous second derivative of the reconstructed function for a specified time value.

27. The method of claim 26, further comprising the act of determining whether the second derivative of the reconstructed function for each pixel has a zero crossing, wherein the presence of the zero crossing indicates a defective pixel and the absence of the zero crossing indicates a defect-free pixel.

28. The method of claim 27, further comprising the act of converting the logarithm of the zero crossing time of the second derivative of the reconstructed function into a linear time domain for defective pixels, assigning a reserved value for defect-free pixels, and using the reserved value and the converted zero crossing time for each pixel to generate a defect map array that uses a first color value for defective pixels and a second color value for defect-free pixels.

29. The method of claim 18, further comprising the act of generating a reference polynomial and subtracts the reconstructed function associated with each pixel in said portion of plurality of pixels from the reference polynomial to generate a contrast curve, wherein a peak in the contrast curve indicates the presence of a subsurface defect.

30. The method of claim 18, further comprising the step of fitting a first polynomial to a first portion of the data array and a second polynomial to a second portion of the data array to generate the reconstructed function.

31. The method of claim 18, further comprising the act of dividing the data array into an early region, an intermediate region, and a late region and fits a first polynomial to the early region, a second polynomial to the intermediate region, and a third polynomial to the late region to generate the reconstructed function.

32. The method of claim 18, further comprising the act of storing the coefficient array in a memory.

33. The method of claim 32, wherein the coefficient array is stored in the memory in a file having a size that is independent of the number of images obtained by the camera.

* * * * *

UNITED STATES PATENT AND TRADEMARK OFFICE
CERTIFICATE OF CORRECTION

PATENT NO.   : 6,751,342 B2
DATED        : July 15, 2004
INVENTOR(S)  : Shepard

It is certified that error appears in the above-identified patent and that said Letters Patent is hereby corrected as shown below:

Column 23,
Line 66, change "at least two different images" to -- at least two spatially different images --.

Signed and Sealed this

Twenty-second Day of March, 2005

JON W. DUDAS
*Director of the United States Patent and Trademark Office*